(12) United States Patent
Barden et al.

(10) Patent No.: US 9,566,318 B2
(45) Date of Patent: Feb. 14, 2017

(54) COMBINATION THERAPY

(75) Inventors: Julian Alexander Barden, North Ryde (AU); Angus Gidley-Baird, North Ryde (AU)

(73) Assignee: Biosceptre (Aust) Pty Ltd (AU)

( * ) Notice: Subject to any disclaimer, the term of this patent is extended or adjusted under 35 U.S.C. 154(b) by 347 days.

(21) Appl. No.: 14/129,240

(22) PCT Filed: Jul. 2, 2012

(86) PCT No.: PCT/AU2012/000795
§ 371 (c)(1),
(2), (4) Date: Apr. 7, 2014

(87) PCT Pub. No.: WO2013/003895
PCT Pub. Date: Jan. 10, 2013

(65) Prior Publication Data
US 2015/0004179 A1 Jan. 1, 2015

(30) Foreign Application Priority Data
Jul. 1, 2011 (AU) ................ 2011902623

(51) Int. Cl.
*A61K 38/16* (2006.01)
*C07K 14/435* (2006.01)
*A61K 39/00* (2006.01)

(52) U.S. Cl.
CPC .................. *A61K 39/0011* (2013.01)

(58) Field of Classification Search
None
See application file for complete search history.

(56) References Cited

U.S. PATENT DOCUMENTS

| | | |
|---|---|---|
| 6,133,434 A | 10/2000 | Buell et al. |
| 6,303,338 B1 | 10/2001 | Ni et al. |
| 6,306,393 B1 | 10/2001 | Goldenberg et al. |
| 6,329,503 B1 | 12/2001 | Afar et al. |
| 6,709,832 B1 | 3/2004 | Von Knebel Doeberitz |
| 7,183,064 B1 | 2/2007 | Slater et al. |
| 7,326,415 B2 | 2/2008 | Barden et al. |
| 7,531,171 B2 | 5/2009 | Barden et al. |
| 7,767,789 B2 | 8/2010 | Gorodeski et al. |
| 7,888,473 B2 | 2/2011 | Barden et al. |
| 8,067,550 B2 | 11/2011 | Barden et al. |
| 8,080,635 B2 | 12/2011 | Barden et al. |
| 8,293,491 B2 | 10/2012 | Gidley-Baird et al. |
| 8,399,617 B2 | 3/2013 | Barden et al. |
| 8,440,186 B2 | 5/2013 | Barden et al. |
| 8,597,643 B2 | 12/2013 | Barden et al. |
| 8,658,385 B2 | 2/2014 | Gidley-Baird et al. |
| 8,709,425 B2 | 4/2014 | Barden et al. |
| 2004/0067542 A1 | 4/2004 | Barden et al. |
| 2007/0020706 A1 | 1/2007 | Gorodeski et al. |
| 2007/0248963 A1 | 10/2007 | Slater et al. |
| 2008/0131438 A1 | 6/2008 | Barden et al. |
| 2008/0227122 A1 | 9/2008 | Barden et al. |
| 2009/0215727 A1 | 8/2009 | Douglas |
| 2010/0036101 A1 | 2/2010 | Gidley-Baird et al. |
| 2011/0111431 A1 | 5/2011 | Slater et al. |
| 2012/0282278 A1 | 11/2012 | Barden et al. |
| 2012/0329076 A1 | 12/2012 | Barden et al. |
| 2013/0266592 A1 | 10/2013 | Barden et al. |
| 2013/0273085 A1 | 10/2013 | Barden et al. |
| 2014/0135475 A1 | 5/2014 | Barden et al. |
| 2014/0323693 A1 | 10/2014 | Barden et al. |

FOREIGN PATENT DOCUMENTS

| | | |
|---|---|---|
| AU | 64184/98 B2 | 10/1998 |
| CA | 2284859 C | 1/2007 |
| EP | 1006186 A1 | 10/1998 |
| WO | WO 92/16558 A1 | 10/1992 |
| WO | WO 95/33048 A2 | 12/1995 |
| WO | WO 97/06256 A2 | 2/1997 |
| WO | WO 97/41222 A1 | 11/1997 |
| WO | WO 98/42835 A1 | 10/1998 |
| WO | WO 00/50458 A1 | 8/2000 |
| WO | WO 01/00041 A1 | 1/2001 |
| WO | WO 01/06259 A1 | 1/2001 |
| WO | WO 01/30964 A2 | 5/2001 |
| WO | WO 02/48395 A1 | 6/2002 |
| WO | WO 02/057306 A1 | 7/2002 |
| WO | WO 03/020762 A1 | 3/2003 |
| WO | WO 2004/092384 A2 | 10/2004 |
| WO | WO 2007/027957 A2 | 3/2007 |
| WO | WO 2008/043145 A2 | 4/2008 |
| WO | WO 2008/043146 A1 | 4/2008 |
| WO | WO 2009/033233 A1 | 3/2009 |
| WO | WO 2009/033234 A1 | 3/2009 |
| WO | WO 2010/000041 A1 | 1/2010 |
| WO | WO 2011/020155 A1 | 2/2011 |
| WO | WO 2011/075789 A1 | 6/2011 |
| WO | WO 2011/131472 A1 | 10/2011 |

(Continued)

OTHER PUBLICATIONS

U.S. Appl. No. 13/391,619, Notice of Allowance mailed Apr. 27, 2015.
U.S. Appl. No. 14/067,873, Requirement for Restriction/Election mailed Jun. 4, 2015.
U.S. Appl. No. 13/391,619, Requirement for Restriction/Election mailed Aug. 5, 2014.
U.S. Appl. No. 13/841,692, Requirement for Restriction/Election mailed Sep. 16, 2014.
U.S. Appl. No. 60/686,770, filed Jun. 2, 2005, Gorodeski et al.
U.S. Appl. No. 60/778,993, filed Mar. 3, 2006, Gorodeski et al.
Ayyanathan et al., "Cloning and chromosomal localisation of the human P2Y1 purinoceptor," Biochem Biophys Res Commun, 218(3):783-788, (1996).

(Continued)

*Primary Examiner* — Christine J Saoud
*Assistant Examiner* — Jon M Lockard
(74) *Attorney, Agent, or Firm* — Alston & Bird LLP

(57) ABSTRACT

The invention relates to producing humoral response to P2X7 receptors in individuals having cancer, and to minimizing the progression of cancer in said individuals.

9 Claims, 1 Drawing Sheet

(56) References Cited

FOREIGN PATENT DOCUMENTS

| WO | WO 2012/031333 A1 | 3/2012 |
|---|---|---|
| WO | WO 2013/003895 A1 | 1/2013 |

OTHER PUBLICATIONS

Barden et al., "Specific detection of non-functional human P2X7 receptos in HEK293 cells and B-lymphocytes," FEBS Letters, 538:159-162, (2003).
Bird et al., "Single-Chain Antigen-Binding Proteins," Science, 242(4877):423-426, (1988).
Bowler et al., "Identification and cloning of human P2U purinoceptor present in osteoclastoma, bone, and osteoblasts," J Bone Min Res, 10(7):1137-1145, (1995).
Buell et al., "P2X receptors: am emerging channel family," Eur J Neurosci., 8:2221-2228, (1996).
Buell et al.,"Blockade of Human P2X7 Receptor Function With a Monoclonal Antibody," Blood, 92:3521-3528, (1998).
Burnstock et al., "P2 Purinergic Receptors: Modulation of Cell Function and Therapeutic Potential," J Pharm Exp Therap, 295:862-869, (2000).
Casset et al., "A peptide mimetic of an anti-CD4 monoclonal antibody by rational design," Biochemical and Biophysical Research Communications, 307:198-205, (2003).
Chan et al., "Localization of P2X1 purinoceptors by autoradiography and immunohistochemistry in rat kidneys," Am J Physiol Renal Physiol, 274(4(2)): F799-804, (1998).
Cheewatrakoolpong et al., "Identification and characterization of splice variants of the human P2X7 ATP channel," Biochem Biophys Res Comm., 332:17-27, (2005).
Chessell et al., "Dynamics of P2X7 receptor pore dilation: pharmacological and functional consequences," Drug Dev Res, 53(2-3):60-65, (2001).
Colman, "Effects of amino acid sequence changes on antibody-antigen interactions," Research in Immunology, A Structural View of Immune Recognition by Antibodies, 55th Forum in Immunology, 145:33-36, (1994).
Communi et al., "Cloning and Functional Expression of a Human Uridine Nucleotide Receptor," J Biol Chem, 270(52): 30849-30852, (1995).
Communi et al., "Cloning, Functional Expression and Tissue Distribution of the Human P2Y6 Receptor," Biochem Biophys Res Commun, 222:303-308, (1996).
Dangl et al., "Rapid Isolation of Cloned Isotype Switch Variants Using Fluorescence Activated Cell Sorting," Cytometry, 2:395-401, (1982).
DeRisi et al., "Exploring the Metabolic and Genetic Control of Gene Expression on a Genomic Scale," Science, 278: 680-686, (1997).
Di Virgilio et al., "Responses of mouse lymphocytes to extracellular adenosine 5'triphosphaste (ATP)," J Immunol 143:1955-1960, (1989).
Di Virgiolio et al., "Purinergic P2X7 receptor: a pivotal role in inflammation and immunomodulation," Drug Dev Res, 45:207-213, (1998).
Dixon et al., "Extracellular nucleotides stimulate proliferation in MCF-7 breast cancer cells via P2-purinoceptors," Br J Cancer, 75(1):34-39, (1997).
Dubyak et al., "Signal transduction via P2-purinergic receptors for extracellular ATP and other nucleotides," Am. J Physiol 265:C577-C606,(1993).
European Search Report of Sep. 18, 2008 for application EP08156593 (published as EP1961767).
Feng et al., "A truncated P2X7 receptor variant (P2X7-j) endogenously expressed in cervical cancer cells antagonizes the full-length P2X7 receptor through hetero-oligomerization," J Biol Chem, 281:17228-17237, (2006).
Feng et al., "ATP stimulates GRK-3 phosphorylation and 3-arrestin-2-dependent internalization of P2X7 receptor," Am J Physiol Cell Physiol, 288:C1342-C1356, (2005).

Feng et al., "Endogenously Expressed Truncated P2X, Receptor Lacking the C-Terminal (P2X7-RTr) is Preferentially Upregulated in Epithelial Cancer Cells and Fails to Mediate Ligand-Induced Pore Formation and Apoptosis," 10th Symposium European Society for the Study of Purine and Pyrimidine Metabolism in Man, Abstract and Programme, Jun. 8-11, 2005.
Feng et al., "Endogenously Expressed Truncated P2X7 Receptor Lacking the C-Terminus is Preferentially Upregulated in Epithelial Cancer Cells and Fails to Mediate Ligand-Induced Pore Formation and Apoptosis," Nucleosides, Nucleotides and Nucleic Acids, 25:1271-1276, (2006).
Ferrari et al., "P2Z purinoreceptor ligation induces activation of caspases with distinct roles in apoptotic and necrotic alterations of cell death," FEBS Lett., 447:71-75, (1999).
Ferrari et al., "ATP-mediated cytoxicity in microglial cells," Neuropharmacology, 36 (9):1295-1301, (1997).
Foster et al., "Cellular and molecular pathology of prostate cancer precursors," Scand J Urol Nephrol Suppl.,34(205):19-43, (2000).
Galfre et al., "Antibodies to major histocompatability antigens produced by hybrid cell lines," Nature, 266:550-552, (1977).
Galfre et al., "Rat x rat hybrid myelomas and a monoclonal anti-Fd portion of mouse IgG," Nature, 277:131-133, (1979).
Gefter et al., "A simple method for polyethylene glycol-promoted hybridization of mouse myeloma cells," Somatic Cell Genet., 3(2):231, (1977).
GenBank: Accession No. Y09561, versions Y09561.1, "H. sapiens mRNA for P2X7 receptor". [Retrieved from the Internet May 24, 2011: <URL: http://www.ncbi.nlm.nih.gov/nuccore/y09561 >].
Georgiou et al., "Human Epidermal and Monocyte-Derived Langerhans Cells Express Functional P2X7 Receptors," J Invest Dermatology, 125:482-490, (2005).
Giusti et al., "Somatic diversification of S107 from an antiphosphocholine to an anti-DNA autoantibody is due to a single base change in its heavy chain variable region," PNAS, 84:2926-2930, (1987).
Greenbaum et al., "Comparing protein abundance and mRNA expression levels on a genomic scale," Genome Biology, 4(9):117.1-117.8, (2003).
Greig et al., "Expression of Purinergic Receptors in Non-melanoma Skin Cancers and Their Functional Roles in A431 Cells," J Invest Dermatol, 121:315-327, (2003).
Groschel-Stewart et al., "Localisation of P2X5 and P2X7 receptors by immunohistochemistry in rat stratified squamous epithelia," Cell Tissue Res, 296:599-605, (1999).
Gu et al, "A Glu-496 to Ala Polymorphism leads to loss of function of the human P2X7 receptor," J Biol Chem, 276(14):11135-11142, (2001).
Gu et al., "An Arg307 to Gln Polymorphism within the ATP-binding Site Causes Loss of Function of the Human P2X7 Receptor," J Biol Chem, 279 (30):31287-31295, (2004).
Gu et al., "Expression of P2X7 purinoceptors on human lymphocytes and monocytes: evidence for nonfunctional P2X 7 receptors," Am J Physiol Cell Physiol, 279:C1189-C1197, (2000).
Gussow et al., "Humanization of Monoclonal Antibodies," Methods in Enzymology, 203:99-121, (1991).
Hansen et al., "Structural Motif and Characteristics of the Extracellular Domain of P2X Receptors," Biochem and Biophys Res Comm, 236(3):670-675, (1997).
Hansen et al., "The distribution of single P (2×1)—receptor clusters on smooth muscle cells in relation to nerve varicosities in the rat urinary bladder," J Neurocytol, 27(7): 529-539, (1998).
Holliger et al., "'Diabodies': Small bivalent and bispecific antibody fragments," Proc. Natl. Aced Sci. USA, 90:6444-6448, (1993).
Hopfner et al, "Expression of functional P2-purinergic receptors in primary cultures of human colorectal carcinoma cells," Biochem and Biophys Res Comm, 251:811-817, (1998).
Humphrey, "Gleason grading and prognostic factors in carcinoma of the prostate," Modern Pathology, 17:292-306, (2004).
Huston et al., "Protein engineering of antibody binding sites: Recovery of specific activity in an anti-digoxin single-chain Fv analogue produced in *Escherichia coli*," Proc. Natl. Acad. Sci. USA, 85:5879-5883, (1988).

(56) References Cited

OTHER PUBLICATIONS

Jacob et al., "Cytogenetic Profile of Chronic Myeloid Leukemias," Indian J Cancer, 39(2):61-65, (2002).
Jameison et al., "Extracellular ATP causes loss of L-selectin from human lymphocytes via occupancy of P2Z purinoceptors," J Cell Physiol, 166:637-642 (1996).
Janssens et al., "Effects of extracellular nucleotides and nucleosides on prostate carcinoma cells," Br J Pharmacol., 132: 536-46, (2001).
Jantzen et al., "Evidence for Two Distinct G-protein-coupled ADP Receptors Mediating Platelet Activation," Thromb and Haemost, 81:111-117, (1999).
Jones, "Critically assessing the state-of-the-art in protein structure prediction,"Pharmacogenomics Journal, 1:126-134, (2001).
Katzur et al., "Expression and responsiveness of P2Y2 receptors in human endometrial cancer cell lines," J Clin Endocrinol Metab., 84(11): 4085-4091, (1999).
Kennedy et al., "The discovery and development of P2 receptor subtypes," J Auto Nerv Syst, 81:158-163, (2000).
Kim et al., "Differential Assembly of Rat Purinergic P2X7 Receptor in Immune Cells of the Brain and Periphery," J Biol Chem, 276(26):23262-23267, (2001).
King et al., "Metabotropic receptors for ATP and UTP: exploring the correspondence between native and recombinant nucleotide receptors," TiPS, 19: 506-514, (1998).
Kishore et al., "Cellular localisation of P2Y2 purinoceptor in rat renal inner medulla and lung," Am J Physiol Renal Physiol, 278: F43-F51, (2000).
La Sala at al., "Alerting and tuning the immune response by extracellular Nucleotides," J Leukoc Biol, 73:339-343, (2003).
Lee et al., "P2X receptor immunoreactivity in the male genital organs of the rat," Cell Tissue Res, 300(2): 321-330, (2000).
Li et al., "P2X7 Receptor: A Novel Biomarker of Uterine Epithelial Cancers," Cancer Epidemiol Biomarkers Prev, 15(10):1906-1913, (2006).
MacCallum et al, "Antibody-antigen Interactions: Contact Analysis and Binding Site Topography," J. Mol. Biol., 262:732-745, (1996).
Mager et al., "Prediction of the confirmation of the human P2X7 receptor," Letts Drug Des Discov, 3(10):675-682, (2006).
Maier et al., "Cloning of P2Y6 cDNAs and Identification of a Pseudogene: Comparison of P2Y Receptor Subtype Expression in Bone and Brain Tissues," Biochem and Biophys Res Comm, 237:297-302, (1997).
Mariuzza et al., "The structural basis of antigen-antibody recognition," Annual Review of Biophysics and Biophysical Chemistry, 16:139-159, (1987).
Mauro et al., "Chronic myelogenous leukaemia," Curr Opin Oncol, 13(1):3-7, (2001).
Meeker et al., "An additional breakpoint region in the BCL-1 locus associated with the t(11:14)(q13;q32) translocation of B-lymphocytic malignancy," Blood, 74:1801-1806, (1989).
Nawa et al., "Frequent loss of expression or aberrant alternative splicing of P2XM, a p53—inducible gene, in soft-tissue tumours," Br J Cancer, 80(8):1185-89, (1999).
Ngo et al "Computational complexity, protein structure prediction, and the Levinthal paradox," In Merz and Le Grand (eds), The protein folding problem and tertiary structure prediction, Birkhauser: Boston, pp. 491-495, (1994).
Nihei et al., "Pharmacologic properties of P2z/P2X7 receptor characterized in murine dendritic cells: role on the induction of apoptosis", Blood, 96(3)996-1005, (2000).
Parr et al., "Cloning and expression of a human P2U nucleotide receptor, a target for cystic fibrosis pharmacotherapy," Proc. Natl. Acad. Sci. USA, 91:3275-3279, (1994).
Paul, Fundamental Immunology, 3rd Edition, Raven Press, New York, Chapt. 9, pp. 292-295 (1993).
Paul, Fundamental Immunology, Lippincott Williams & Wilkins, p. 107, (1998).
PCT International Preliminary Examination Report of Mar. 14, 2003 for application PCT/AU2001/001614.
PCT International Preliminary Examination Report of May 1, 2003 for application PCT/AU02/00061.
PCT International Preliminary Examination Report of Aug. 1, 2001 for application PCT/AU00/00363.
PCT International Preliminary Examination Report of Dec. 17, 2003 for application PCT/AU02/001204.
PCT International Preliminary Report on Patentability of Jan. 5, 2011 for application PCT/AU09/000869.
PCT International Preliminary Report on Patentability of Jan. 16, 2014 for application PCT/AU2012/000795.
PCT International Preliminary Report on Patentability of Mar. 12, 2013 for application PCT/AU2011/001166.
PCT International Preliminary Report on Patentability of Mar. 16, 2010 for application PCT/AU08/001364.
PCT International Preliminary Report on Patentability of Mar. 16, 2010 for application PCT/AU08/001365.
PCT International Preliminary Report on Patentability of Apr. 15, 2009 for application PCT/AU07/001540.
PCT International Preliminary Report on Patentability of Apr. 15, 2009 for application PCT/AU07/001541.
PCT International Preliminary Report on Patentability of Jun. 26, 2012 for application PCT/AU2010/001741.
PCT International Search Report for application PCT/AU2010/001741 mailed Feb. 11, 2011.
PCT International Search Report of Feb. 5, 2002 for application PCT/AU2001/001614.
PCT International Search Report of Apr. 2, 2002 for application PCT/AU02/00061.
PCT International Search Report of Jul. 21, 2000 for application PCT/AU00/00363.
PCT International Search Report of Aug. 7, 2009 for application PCT/AU09/000869.
PCT International Search Report of Sep. 20, 2012 for applicatin PCT/AU2012/000795.
PCT International Search Report of Sep. 22, 2010 for application PCT/AU10/001070.
PCT International Search Report of Oct. 14, 2002 for application PCT/AU02/001204.
PCT International Search Report of Oct. 27, 2008 for application PCT/AU08/001364.
PCT International Search Report of Nov. 4, 2011 for application PCT/AU2011/001166.
PCT International Search Report of Nov. 9, 2007 for application PCT/AU07/001541.
PCT International Search Report of Nov. 21, 2008 for application PCT/AU08/001365.
PCT International Search Report of Nov. 2007 for application PCT/AU07/001540.
Peng et al., "P2Z purinoceptor, a special receptor for apoptosis induced by ATP in human leukemic lymphocytes," Chinese Med J, 112(4):356-362, (1999).
Perou et al., "Distinctive gene expression patterns in human mammary epithelial cells and breast cancers," Proc. Natl. Acad. Sci. USA, 96:9212-9217, (1999).
Poljak et al., "Production and structure of diabodies," Structure, 2:1121-1123, (1994).
Ralevic et al., "Receptors for Purines and Pyrimidines," Pharmacol Rev., 50(3):413-492, (1998).
Rassendren et al., "The permeabilizing ATP receptor, P2X7: Cloning and expression of a human cDNA," J Biol Chem, 272(9):5482-5486, (1997).
Ray et al., "Purinergic receptor distribution in endothelial cells in blood vessels: a basis for selection of coronary artery grafts," Atherosclerosis, 162:55-61, (2002).
Romagnoli et al., "Recent progress in the discovery of antagonists acting at P2X7 receptor," Expert Opinions Ther. Patents, 15(3):271-287, (2005).
Roman et al., "Cloning and Pharmacological Characterization of the Dog P2X7 Receptor," British Journal of Pharmacology, 158:1513-1526, (2009).
Rudikoff et al., "Single amino acid substitution altering antigen-binding specificity," PNAS, 79:1979-1983, (1982).

(56) References Cited

OTHER PUBLICATIONS

Sauer et al., "Calcium-dependence of hydrogen peroxide-induced c-fos expression and growth stimulation of multicellular prostate tumour spheroids," FEBS Lett, 419: 201-205, (1997).
Schultze-Mosgau et al., "Characterization of calcium-mobilizing, purinergic P2Y2 receptors in human ovarian cancer cells," Mol Human Reproduct., 6(5): 435-442, (2000).
Slater et al. "Early prostate cancer detected using expression of non-functional cytolytic P2X7 receptors," Histopathology, 44:206-215, (2004).
Slater et al., "Detection of preneoplasia in histologically normal prostate biopsies," Prost Cancer Prostat Dis, 4:92-96, (2001).
Slater et al., "Differentiation between cancerous and normal hyperplastic lobules in breast lesions," Breast Cancer Res Treat, 83:1-10, (2004).
Slater et al., "Expression of the apoptotic calcium channel P2X7 in the glandular epithelium is a marker for early prostate cancer and correlates with increasing PSA levels," J Mol Histol., 36:159-165, (2005).
Slater et al., "Increased expression of apoptotic markers in melanoma," Melanoma Res, 13(2):137-145, (2003).
Slater et al., "Markers for the development of early prostate cancer," J Pathol,199:368-377, (2003).
Sluyter et al., "Extracellular ATP increases cation fluxes in human erthrocytes by activation of the P2X7 receptor," J Biol Chem, 279(43):44749-44756, (2004).
Spieker-Polet et al., "Rabbit monoclonal antibodies: Generating a fusion partner to produce rabbit-rabbit hybridomas," Proc. Natl. Acad. Sci USA, 92:9348-9352, (1995).
Supplementary European Search Report and European Search Opinion for application EP08800000 (published as EP2201026) mailed Oct. 29, 2012.
Supplementary European Search Report and European Search Opinion for application EP09771858 (published as EP2318438) mailed Oct. 24, 2012.
Supplementary European Search Report and European Search Opinion for application EP10838429 (published as EP2516470) mailed Apr. 13, 2013.
Supplementary European Search Report of Mar. 4, 2011 for application EP01270623 (published as EP1352085).
Supplementary European Search Report of May 21, 2010 for application EP07815345 (published as EP2082032).
Supplementary European Search Report of Aug. 16, 2010 for application EP08800001 (published as EP2201377).
Supplementary European Search Report of Nov. 8, 2002 for application EP0091860 (published as EP1179183).
Supplementary European Search Report of Apr. 29, 2005 for application EP02715313 (published as EP1360203).
Surprenant et al., "The cytosolic P2Z receptor for extracellular ATP identified as a P2X receptor (P2X7)," Science, 272:735-738, (1996).
Tockman et al., "Considerations in Bringing a Cancer Biomarker to Clinical Application," Cancer Res, 52:2711s-2718s, (1992).
Torres et al., "Hetero-oligomeric Assembly of P2X Receptor Subunits," J Biol Chem, 273(10):6653-6659, (1999).
Tosatto et al., "Large-Scale Prediction of Protein Structure and Function from Sequence," Current Pharmaceutical Design, 12:2067-2086, (2006).
U.S. Appl. No. 10/019,356 (now U.S. Pat. No. 7,183,064), Final Office Action mailed May 9, 2006.
U.S. Appl. No. 10/019,356 (now U.S. Pat. No. 7,183,064), Non-Final Office Action mailed Jul. 19, 2005.
U.S. Appl. No. 10/019,356 (now U.S. Pat. No. 7,183,064), Notice of Allowance mailed Oct. 11, 2006.
U.S. Appl. No. 10/019,356 (now U.S. Pat. No. 7,183,064), Requirement for Restriction/Election mailed Mar. 18, 2005.
U.S. Appl. No. 10/450,205 (now Abandoned, Publication No. 2004/0067542), Final Office Action mailed Sep. 7, 2007.
U.S. Appl. No. 10/450,205 (now Abandoned, Publication No. 2004/0067542), Non-Final Office Action mailed Dec. 19, 2006.
U.S. Appl. No. 10/450,205 (now Abandoned, Publication No. 2004/0067542), Requirement for Restriction/Election mailed Sep. 6, 2006.
U.S. Appl. No. 10/622,313 (now U.S. Pat. No. 7,326,415), Non-Final Office Action mailed Nov. 30, 2006.
U.S. Appl. No. 10/622,313 (now U.S. Pat. No. 7,326,415), Notice of Allowance and Examiner Interview Summary Record mailed Sep. 5, 2007.
U.S. Appl. No. 10/622,313 (now U.S. Pat. No. 7,326,415), Requirement for Restriction/Election mailed Jun. 16, 2006.
U.S. Appl. No. 11/566,472 (now Abandoned, Publication No. 2007/0248963), Examiner Interview Summary Record mailed Dec. 30, 2009.
U.S. Appl. No. 11/566,472 (now Abandoned, Publication No. 2007/0248963), Final Office Action mailed Jan. 12, 2009.
U.S. Appl. No. 11/566,472 (now Abandoned, Publication No. 2007/0248963), Final Office Action mailed Mar. 9, 2010.
U.S. Appl. No. 11/566,472 (now Abandoned, Publication No. 2007/0248963), Non-Final Office Action mailed Jun. 16, 2008.
U.S. Appl. No. 11/566,472 (now Abandoned, Publication No. 2007/0248963), Non-Final Office Action mailed Aug. 26, 2009.
U.S. Appl. No. 11/566,472 (now Abandoned, Publication No. 2007/0248963), Requirement for Restriction/Election mailed Dec. 17, 2007.
U.S. Appl. No. 11/968,607 (now U.S. Pat. No. 7,531,171), Non-Final Office Action mailed Sep. 26, 2008.
U.S. Appl. No. 11/968,607 (now U.S. Pat. No. 7,531,171), Notice of Allowance mailed Jan. 9, 2009.
U.S. Appl. No. 11/968,607 (now U.S. Pat. No. 7,531,171), Requirement for Restriction/Election mailed Aug. 19, 2008.
U.S. Appl. No. 12/043,083 (now Abandoned, Publication No. 2008/0227122), Non-Final Office Action mailed Nov. 26, 2010.
U.S. Appl. No. 12/043,083 (now Abandoned, Publication No. 2008/0227122), Notice of Allowance mailed Aug. 5, 2011.
U.S. Appl. No. 12/043,083 (now Abandoned, Publication No. 2008/0227122), Requirement for Restriction/Election mailed Jul. 21, 2010.
U.S. Appl. No. 12/417,989 (now U.S. Pat. No. 7,888,473), Non-Final Office Action mailed Jun. 16, 2010.
U.S. Appl. No. 12/417,989 (now U.S. Pat. No. 7,888,473), Notice of Allowance mailed Sep. 24, 2010.
U.S. Appl. No. 12/445,258 (now Abandoned, Publication No. 2010/0036101), Non-Final Office Action mailed Oct. 18, 2011.
U.S. Appl. No. 12/445,258 (now Abandoned, Publication No. 2010/0036101), Requirement for Restriction/Election mailed May 6, 2011.
U.S. Appl. No. 12/445,273 (now U.S. Pat. No. 8,067,550), Non-Final Office Action mailed Oct. 1, 2010.
U.S. Appl. No. 12/445,273 (now U.S. Pat. No. 8,067,550), Notice of Allowance mailed Mar. 30, 2011.
U.S. Appl. No. 12/445,273 (now U.S. Pat. No. 8,067,550), Notice of Allowance mailed Jul. 8, 2011.
U.S. Appl. No. 12/445,273 (now U.S. Pat. No. 8,067,550), Requirement for Restriction/Election mailed Aug. 9, 2010.
U.S. Appl. No. 12/677,795 (now U.S. Pat. No. 8,293,491), Notice of Allowance mailed Jun. 22, 2012.
U.S. Appl. No. 12/677,795 (now U.S. Pat. No. 8,293,491), Restriction/Election Requirement mailed Oct. 12, 2011.
U.S. Appl. No. 12/677,799, Non-Final Office Action mailed Jun. 21, 2012.
U.S. Appl. No. 12/677,799, Notice of Allowance and Examiner Interview Summary Record mailed Dec. 10, 2012.
U.S. Appl. No. 12/677,799, Notice of Allowance mailed Jan. 9, 2013.
U.S. Appl. No. 12/677,799, Requirement for Restriction/Election mailed Feb. 23, 2012.
U.S. Appl. No. 12/878,865 (now Abandoned, Publication No. 2011/0111431), Non-Final Office Action mailed Oct. 20, 2011.
U.S. Appl. No. 12/878,865 (now Abandoned, Publication No. 2011/0111431), Requirement for Restriction/Election mailed Mar. 25, 2011.
U.S. Appl. No. 12/975,341 (now U.S. Pat. No. 8,080,635), Non-Final Office Action mailed Mar. 24, 2011.

(56) References Cited

OTHER PUBLICATIONS

U.S. Appl. No. 12/975,341 (now U.S. Pat. No. 8,080,635), Notice of Allowance mailed Aug. 17, 2011.
U.S. Appl. No. 13/002,647, Non-Final Office Action mailed Dec. 20, 2012.
U.S. Appl. No. 13/002,647, Notice of Allowance mailed Aug. 2, 2013.
U.S. Appl. No. 13/002,647, Requirement for Restriction/Election mailed Aug. 7, 2012.
U.S. Appl. No. 13/298,222, Final Office Action mailed Sep. 7, 2012.
U.S. Appl. No. 13/298,222, Non-Final Office Action mailed Feb. 13, 2012.
U.S. Appl. No. 13/298,222, Notice of Allowance and Examiner Interview Summary Record mailed Nov. 27, 2012.
U.S. Appl. No. 13/518,382, Final Office Action mailed Dec. 30, 2013.
U.S. Appl. No. 13/518,382, Non-Final Office Action mailed Jun. 18, 2013.
U.S. Appl. No. 13/518,382, Non-Final Office Action mailed Sep. 18, 2013.
U.S. Appl. No. 13/518,382, Notice of Allowance and Examiner Initiated Interview Summary mailed May 5, 2014.
U.S. Appl. No. 13/518,382, Requirement for Restriction/Election mailed Mar. 21, 2013.
U.S. Appl. No. 13/626,833, Non-Final Office Action mailed Jun. 13, 2013.
U.S. Appl. No. 13/626,833, Notice of Allowance and Examiner Initiated Interview Summary mailed Sep. 27, 2013.
U.S. Appl. No. 13/766,630, Non-Final Office Action mailed Aug. 19, 2013.
U.S. Appl. No. 13/766,630, Notice of Allowance and Examiner Initated Interview Summary mailed Dec. 11, 2013.
U.S. Appl. No. 13/821,555, Requirement for Restriction/Election mailed Jun. 19, 2014.
U.S. Appl. No. 12/677,795 (now U.S. Pat. No. 8,293,491), Non-Final Office Action mailed Feb. 29, 2012.
Uniprot entry Q4VKI0_Human P2X7 Isoform E, UniProt Consortium, (2005).
Uniprot entry Q4VKI0_Human P2X7 Isoform F, UniProt Consortium, (2005).
Uniprot sequence entry: Accession No. Q4VKH8, "P2X7 isoform H," Jul. 2005. [Retrieved from the Internet Sep. 9, 2013: <URL: http:// www.ncbi.nlm.nih.gov/protein/Q4VKH8>].
Uniprot sequence entry: Accession No. Q4VKH9, "P2X7 isoform G," Jul. 2005. [Retrieved from the Internet Sep. 9, 2013: <URL: http:// www.ncbi.nlm.nih.gov/protein/Q4VKH9>].
Uniprot sequence entry: Accession No. Q4VKI2, "P2X7 isoform D," Jul. 2005. [Retrieved from the Internet Sep. 9, 2013: <URL: http:// www.ncbi.nlm.nih.gov/protein/Q4VKI2>].
Uniprot sequence entry: Accession No. Q4VKI4, "P2X7 isoform B," Jul. 2005. [Retrieved from the Internet Sep. 9, 2013: <URL: http:// www.ncbi.nlm.nih.gov/protein/Q4VKI4>].
Urano et al., "Cloning of P2XM, a novel human P2X receptor gene regulated by p53," Cancer Res, 57:3281-87, (1997).
Virginio et al., "Kinetics of cell lysis, dye uptake and permeability changes in cells expressing the rat P2X7 receptor," J Physiol. 519(2):335-346, (1999).

von Kugelgen et al., "Molecular Pharmacology of P2Y-receptors," Naunyn Scmiedebergs Arch Pharmacol, 362:(4-5)310-323, (2000).
Vulchanova et al., "Immunohistochemical study of the P2X2 and P2X3 receptor subunits in rat and monkey sensory neurons and their central terminals," Neuropharmacol, 36(9):1229-1242, (1997).
Wagstaff et al ., "Extracellular ATP activates multiple signalling pathways and potentiates growth factor-induced c-fos gene expression in MCF-7 breast cancer cells," Carcinogenesis 21(12):2175-2181, (2000).
Wang et al., "P2X7 receptor-mediated apoptosis of human cervical epithelial cells," Am. J Physiol, 287:1349-1358, (2004).
Ward et al., "Binding activities of a repertoire of single immunoglobulin variable domains secreted from *Escherichia coli*," Nature 341:544-546, (1989).
Wasilenko et al., "Calcium signaling in prostate cancer cells: Evidence for multiple receptors and enhanced sensitivity to bombesin/GRP," The Prostate 30:167-173 (1997).
Wells "Additivity of mutational effects in proteins," Biochemistry, 29(37):8509-8517, (1990).
White et al., "P2Y purinergic receptors regulate the growth of human melanomas," Cancer Letts, 224:81-91, (2005).
Wiley et al., "A single nucleotide polymorphism is associated with loss of function of the monocyte P2X7 receptor," Blood, 96(11)17, (2000). Abstract.
Wiley et al., "An Ile-568 to Asn polymorphism prevents normal trafficking and function of the human P2X7 receptor," J Biol Chem 278 (19)17108-17113, (2003).
Wiley et al., "Genetic polymorphisms of the human P2X7 receptor and relationship to function," Drug Dev Res, 53(2-3):72-76, (2001).
Williams et al., "Purinergic and pyrimidinergic receptors as potential drug targets," Biochem Pharm, 59:1173-1184, (2000).
Winkler et al., "Changing the antibody binding specificity by single point mutations of an Anti-p24 (HIV-1) antibody," Journal of Immunology, 165:4505-4514, (2000).
Worthington et al., "Point mutations confer loss of ATP-induced human P2X7 receptor function," FEBS Lett, 512:43-46, (2002).
Wurl et al., "High prognostic significance of Mdm2/p53 co-overexpression in soft tissue sarcomas of the extremities," Oncogene,16(9):1183-85, (1998).
Supplementary European Search Report and European Search Opinion for application EP10809371.7 (published as EP2467404) mailed Dec. 21, 2012.
Supplementary European Search Report and European Search Opinion for application EP11822941.8 (published as EP2613808) mailed Jan. 7, 2014.
Supplementary European Search Report and European Search Opinion for application EP12807960.5 (published as EP2726095) mailed Dec. 5, 2014.
U.S. Appl. No. 13/841,692, Non-Final Office Action mailed Feb. 26, 2015.
Muyldermans et al., "Nanobodies: Natural Single-Domain Antibodies," Annu. Rev. Biochem., 82:17.1-17.23, (2013).
U.S. Appl. No. 13/391,619, Non-Final Office Action mailed Dec. 23, 2014.
U.S. Appl. No. 14/218,935, Non-Final Office Action mailed Sep. 11, 2014.
International Search Report for PCT/AU2012/000795 mailed Sep. 20, 2012.

SEQUENCE LISTING

<160> NUMBER OF SEQ ID NOS: 5

<210> SEQ ID NO 1
<211> LENGTH: 595
<212> TYPE: PRT

<213> ORGANISM: Homo sapiens

<400> SEQUENCE: 1

```
Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
        35                  40                  45

Lys Leu Tyr Gln Arg Lys Glu Pro Val Ile Ser Ser Val His Thr Lys
    50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
        115                 120                 125

Cys Ser Ser Asp Arg Gly Cys Lys Lys Gly Trp Met Asp Pro Gln Ser
130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Ile
        195                 200                 205

Leu Pro Gly Leu Asn Ile Thr Cys Thr Phe His Lys Thr Gln Asn Pro
    210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
                245                 250                 255

Tyr Trp Asp Cys Asn Leu Asp Arg Trp Phe His His Cys Arg Pro Lys
            260                 265                 270

Tyr Ser Phe Arg Arg Leu Asp Asp Lys Thr Thr Asn Val Ser Leu Tyr
        275                 280                 285

Pro Gly Tyr Asn Phe Arg Tyr Ala Lys Tyr Tyr Lys Glu Asn Asn Val
    290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
                325                 330                 335

Ile Gly Ser Thr Leu Ser Tyr Phe Gly Leu Ala Ala Val Phe Ile Asp
            340                 345                 350

Phe Leu Ile Asp Thr Tyr Ser Ser Asn Cys Cys Arg Ser His Ile Tyr
        355                 360                 365

Pro Trp Cys Lys Cys Cys Gln Pro Cys Val Val Asn Glu Tyr Tyr Tyr
    370                 375                 380

Arg Lys Lys Cys Glu Ser Ile Val Glu Pro Lys Pro Thr Leu Lys Tyr
385                 390                 395                 400
```

```
Val Ser Phe Val Asp Glu Ser His Ile Arg Met Val Asn Gln Gln Leu
            405                 410                 415

Leu Gly Arg Ser Leu Gln Asp Val Lys Gly Gln Glu Val Pro Arg Pro
        420                 425                 430

Ala Met Asp Phe Thr Asp Leu Ser Arg Leu Pro Leu Ala Leu His Asp
        435                 440                 445

Thr Pro Pro Ile Pro Gly Gln Pro Glu Glu Ile Gln Leu Leu Arg Lys
    450                 455                 460

Glu Ala Thr Pro Arg Ser Arg Asp Ser Pro Val Trp Cys Gln Cys Gly
465                 470                 475                 480

Ser Cys Leu Pro Ser Gln Leu Pro Glu Ser His Arg Cys Leu Glu Glu
                485                 490                 495

Leu Cys Cys Arg Lys Lys Pro Gly Ala Cys Ile Thr Thr Ser Glu Leu
            500                 505                 510

Phe Arg Lys Leu Val Leu Ser Arg His Val Leu Gln Phe Leu Leu Leu
        515                 520                 525

Tyr Gln Glu Pro Leu Leu Ala Leu Asp Val Asp Ser Thr Asn Ser Arg
    530                 535                 540

Leu Arg His Cys Ala Tyr Arg Cys Tyr Ala Thr Trp Arg Phe Gly Ser
545                 550                 555                 560

Gln Asp Met Ala Asp Phe Ala Ile Leu Pro Ser Cys Cys Arg Trp Arg
                565                 570                 575

Ile Arg Lys Glu Phe Pro Lys Ser Glu Gly Gln Tyr Ser Gly Phe Lys
            580                 585                 590

Ser Pro Tyr
        595

<210> SEQ ID NO 2
<211> LENGTH: 17
<212> TYPE: PRT
<213> ORGANISM: Homo sapiens

<400> SEQUENCE: 2

Gly His Asn Tyr Thr Thr Arg Asn Ile Leu Pro Gly Leu Asn Ile Thr
1               5                   10                  15

Cys

<210> SEQ ID NO 3
<211> LENGTH: 17
<212> TYPE: PRT
<213> ORGANISM: Homo sapiens

<400> SEQUENCE: 3

Lys Tyr Tyr Lys Glu Asn Asn Val Glu Lys Arg Thr Leu Ile Lys Val
1               5                   10                  15

Phe

<210> SEQ ID NO 4
<211> LENGTH: 25
<212> TYPE: PRT
<213> ORGANISM: Homo sapiens

<400> SEQUENCE: 4

Gly His Asn Tyr Thr Thr Arg Asn Ile Leu Pro Gly Ala Gly Ala Lys
1               5                   10                  15

Tyr Tyr Lys Glu Asn Asn Val Glu Lys
            20                  25
```

```
<210> SEQ ID NO 5
<211> LENGTH: 26
<212> TYPE: PRT
<213> ORGANISM: Homo sapiens

<400> SEQUENCE: 5

Gly His Asn Tyr Thr Thr Arg Asn Ile Leu Pro Gly Ala Gly Ala Lys
1               5                   10                  15

Tyr Tyr Lys Glu Asn Asn Val Glu Lys Cys
            20                  25
```

COMBINATION THERAPY

FIELD OF THE INVENTION

The invention relates to a method of treating or ameliorating diseases that are associated with non-functional P2X$_7$ receptor expression, including cancer.

BACKGROUND OF THE INVENTION

Purinergic (P2X) receptors are ATP-gated cation—selective channels. Each receptor is made up of three protein subunits or monomers. To date seven separate genes encoding P2X monomers have been identified: P2X$_1$, P2X$_2$, P2X$_3$, P2X$_4$, P2X$_5$, P2X$_6$, P2X$_7$.

P2X$_7$ receptors are of particular interest as the expression of these receptors is understood to be limited to cells having potential to undergo programmed cell death, such as thymocytes, dendritic cells, lymphocytes, macrophages and monocytes. There is some expression of P2X$_7$ receptors in normal homeostasis, such as on erythrocytes and in other cell types such as skin at generally lower levels.

Interestingly, a P2X$_7$ receptor containing a monomer having a cis isomerisation at Pro210 (according to SEQ ID NO: 1) and which has compromised ATP binding function at the affected site or sites has been found on cells that are understood to be unable to undergo programmed cell death, such as pre-neoplastic cells and neoplastic cells. This isoform of the receptor has been referred to as a "non-functional" receptor and describes a form of the receptor unable to extend the operating non-selective calcium channel into an apoptotic pore.

Antibodies generated from immunisation with a peptide including Pro210 bind to non-functional P2X$_7$ receptors at the altered ATP binding site/s formed between adjacent monomers. However, they do not bind to P2X$_7$ receptors capable of binding ATP at any of the three available sites. Accordingly, these antibodies are useful for selectively detecting many forms of carcinoma and haemopoietic cancers and to treatment of some of these conditions.

WO02/057306A1 and WO03/020762A1 discuss a probe in the form of a monoclonal antibody for distinguishing between functional P2X$_7$ receptors, defined as those receptors able to form a non-selective Ca/Na channel that is additionally able to form an apoptotic pore upon extended binding of ATP, and non-functional P2X$_7$ receptors, defined as those receptors able to form the non-selective channel but that are unable to extend opening of the channel to an apoptotic pore.

WO2009/033233 discusses an epitope exposed on non-functional receptors but not functional receptors and antibodies for binding thereto.

There exists a need for an alternative or improved treatment of diseases caused by or associated with non-functional P2X$_7$ receptor expression, such as cancer.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

In certain embodiments there is provided a method for minimising the progression of cancer in an individual who has received a non self antigen binding site for treatment of the cancer, the method including the steps of:

providing an individual who has received a non self antigen binding site for treatment of the cancer;

forming an immune response in the individual to a P2X$_7$ receptor;

thereby minimising the progression of cancer in the individual.

In one form of the above described method, the individual may not have detectable non self antigen binding sites in circulation at the time that the immune response is formed in the individual.

Further, the individual may not have detectable cancer at the time that the immune response is formed in the individual, for example, the cancer may have substantially diminished in size, mass or other physical measure as a consequence of administration of an antigen binding site to the individual at the time that the immune response is formed, particularly to a non functional P2X7 receptor, or to a cancer-associated P2X7 receptor, in the individual.

The immune response may be formed by an immunogen. The immunogen may be provided in the form of a P2X$_7$ receptor, or a fragment of a P2X$_7$ receptor that is capable of inducing an immune response to a P2X$_7$ receptor in the individual.

The immunogen may contain at least one sequence that is capable of being presented on a major histocompatibility complex class II molecule and/or is capable of interacting with a T or B-cell receptor or a B-cell membrane bound-immunoglobulin.

According to the invention, the individual is human, in which case the immunogen is provided in the form of a human P2X$_7$ receptor, or fragment thereof that is capable of inducing an immune response to a P2X$_7$ receptor.

Typically the immune response that is formed in the individual is specific for non-functional P2X$_7$ receptors, in which case antibodies or cellular components that are reactive with non-functional P2X$_7$ receptors (i.e. with one or more sites unable to bind ATP), but not reactive with functional P2X$_7$ receptors (i.e. ATP binding receptors) are formed in the individual.

In a preferred form, the immunogen is provided in an initial administration to the individual, thereby forming a response that includes IgM production.

In a further preferred form, the immunogen, which has been provided in an initial administration to the individual, thereby forming a response that includes IgM production, is administered at a later time, in a further administration to the initial administration, thereby forming a response that includes IgG production. In this embodiment, typically the further administration of immunogen occurs when the level of IgM in circulation in the individual is substantially undetectable.

The immune response may be a humoral and/or cellular response.

A humoral response may include the transformation of B-cells into plasma cells, which secrete antibody, Th2 activation and cytokine production, germinal centre formation and isotype switching, affinity maturation of B-cells and/or memory cell generation.

A cellular response may include activating antigen-specific cytotoxic T-lymphocytes, activating macrophages and natural killer cells and/or stimulating cells to secrete cytokines.

The humoral and/or cellular response formed in the individual may treat or ameliorate a cancer in the individual, or minimise the progression of cancer in the individual.

In the above described embodiments, the antigen binding sites received by the individual may be reactive with any biomarker that is associated with cancer. Examples include antigen binding sites against $P2X_7$, especially, non-functional $P2X_7$, against VEGF, especially VEGF A, C or D, Her-2, CD20 or others. Typically the antigen binding sites received by the individual are reactive with $P2X_7$ receptor, especially a non-functional $P2X_7$ receptor.

In another embodiment there is provided a use of a $P2X_7$ receptor or fragment thereof in the manufacture of a medicament for the treatment of, or for the inhibition of progression of cancer in an individual who has received an anti-$P2X_7$ receptor antigen binding site for treatment of the cancer.

In another embodiment there is provided a composition for treating, or for inhibiting the progression of a cancer in a human including a $P2X_7$ receptor or fragment thereof. Preferably the composition further includes a carrier, excipient or diluent. Preferably, the composition further includes an adjuvant.

In another embodiment there is provided a composition for use in the treatment, or for use in the inhibition, of the progression of a cancer in a human including a $P2X_7$ receptor or fragment thereof. Preferably the composition further includes a physiologically acceptable carrier, excipient or diluent. Preferably, the composition further includes an adjuvant.

In another embodiment, there is provided a composition when used in a method of the invention.

In a preferred form, the composition enables the formation of a primary immune response (including IgM production) upon initial administration of the immunogen to the individual, and a second immune response (including IgG production) upon administration of the immunogen further to the initial administration.

In other embodiments there is provided a kit or composition for treatment of, or for inhibiting the progression of a cancer in a human, the kit including:
  an immunogen capable of causing the formation of an immune response to a human $P2X_7$ receptor when administered to a human;
  an antigen binding site that binds to a biomarker associated with cancer; and
  written instructions for use in a method described above.

In one preferred form, the antigen binding site provided in the kit is reactive with a $P2X_7$ receptor, preferably a non-functional $P2X_7$ receptor.

Without being bound by any theory or mode of action, it is believed that the present invention provides an alternative and/or improved treatment regime for the reason that endogenous immune components such as antibodies and antigen specific cells that arise from immunisation have a longer and greater exposure to cell surface $P2X_7$ receptors, after the administration of antigen binding sites has been completed and the circulating level of non self anti-$P2X_7$ antigen binding sites has become undetectable.

Further, it is believed that $P2X_7$ receptor crowding, as arises when high concentrations of non self or exogenous antibodies are provided in an individual, minimises the level of specific antibody binding to the key $P2X_7$ epitopes that provide for an anti cancer immune response, thereby limiting the efficacy of immunotherapy. The inventors have found that an antibody response arising from immunisation of an individual with immunogen according to the invention described herein provides for an amount, titre or concentration of antibody that does not cause receptor crowding, thereby improving the efficacy of immunotherapy, particularly at a time when cancer in the individual may be substantially undetectable.

In one embodiment there is provided a process for forming a humoral immune response to cancer-associated $P2X_7$ receptors in an individual who has received an anti-cancer antigen antibody for therapy of cancer, including the steps of:
  forming an immune response in the individual to an immunogen in the form of a cancer-associated $P2X_7$ receptor or fragment thereof;
  wherein the immune response is formed in the individual at a time where anti-cancer antigen antibody administered for treatment of cancer is at a level or concentration that is substantially undetectable in the individual; and/or
  the humoral immune response to cancer-associated $P2X_7$ receptors is formed according to an immunisation schedule whereby the amount of antibody formed in the individual to cancer-associated $P2X_7$ receptor is about 0.1 to 25 mg/kg individual.

In another embodiment there is provided a composition for use in forming a humoral immune response to cancer-associated $P2X_7$ receptors in an individual who has received an anti-cancer antigen antibody for therapy of cancer, said composition including an immunogen in the form of a cancer-associated $P2X_7$ receptor or fragment thereof. Preferably the immune response is formed in the individual at a time where anti-cancer antigen antibody administered for treatment of cancer is at a level or concentration that is substantially undetectable in the—individual; and/or the humoral immune response to cancer-associated $P2X_7$ receptors is formed according to an immunisation schedule whereby the amount of antibody formed in the individual to cancer-associated $P2X_7$ receptor is about 0.1 to 25 mg/kg individual.

Further aspects of the present invention and further embodiments of the aspects described in the preceding paragraphs will become apparent from the following description, given by way of example and with reference to the accompanying drawings.

Figure 1:
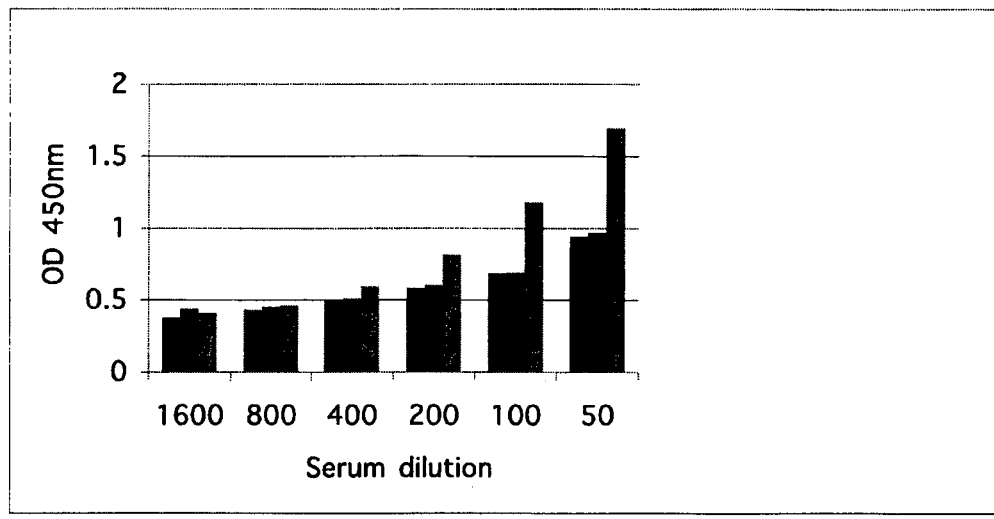
FIG. 1

Patient with moderate tumor burden immunized with peptide GHNYTTRNILPGLNITC coupled to KLH carrier in presence of adjuvant. The ELISA plate carries the peptide and the serum is serially diluted to detect for the presence of antibodies to the peptide. Pre-immune serum (blue), serum obtained immediately pre-boost at Week 4 (red) and serum at Week 13 (9 weeks post boost, green). No antibodies were detected in the pre-boost serum taken 4 weeks post initial immunisation. This is believed to be a consequence of existing tumour mass that binds antibody arising from the immunisation. The Week 13 sample shows a small level of circulating anti-nfP2X_7 antibody response as the tumour burden was decreased. Intermediate measurements taken from Weeks 5 to 12 showed little circulating antibody was present in serum

FIG. 2

Patient with very small residual tumor burden immunized with peptide GHNYTTRNILPGLNITC coupled to KLH carrier in presence of adjuvant. The ELISA plate carries the peptide and the serum is serially diluted to detect for the presence of antibodies to the peptide. Pre-immune serum (blue), serum obtained immediately pre-boost at Week 4 (red) and at Week 5 (1 week post boost, green). Since the patient had little or no residual tumor sink for the circulating antibodies, the levels detected at Week 5 were already much higher than in the patient who had a moderate tumor mass.

DETAILED DESCRIPTION OF THE EMBODIMENTS

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

It will be understood that the invention disclosed and defined in this specification extends to all alternative combinations of two or more of the individual features mentioned or evident from the text or drawings. All of these different combinations constitute various alternative aspects of the invention.

As used herein, except where the context requires otherwise, the term "comprise" and variations of the term, such as "comprising", "comprises" and "comprised", are not intended to exclude further additives, components, integers or steps.

All of the patents and publications referred to herein are incorporated by reference in their entirety.

For purposes of interpreting this specification, the following definitions will generally apply and whenever appropriate, terms used in the singular will also include the plural and vice versa. In the event that any definition set forth conflicts with any document incorporated herein by reference, the definition set forth below shall prevail.

"Purinergic receptor" generally refers to a receptor that uses a purine (such as ATP) as a ligand.

"$P2X_7$ receptor" generally refers to a purinergic receptor formed from three protein subunits or monomers, with at least one of the monomers having an amino acid sequence substantially as shown in SEQ ID No:1. To the extent that $P2X_7$ receptor is formed from three monomers, it is a "trimer" or "trimeric". "$P2X_7$ receptor" may be a functional or non-functional receptor as described below. "$P2X_7$ receptor" encompasses naturally occurring variants of $P2X_7$ receptor, e.g., wherein the $P2X_7$ monomers are splice variants, allelic variants and isoforms including naturally-occurring truncated or secreted forms of the monomers forming the $P2X_7$ receptor (e.g., a form consisting of the extracellular domain sequence or truncated form of it), naturally-occurring variant forms (e.g., alternatively spliced forms) and naturally-occurring allelic variants. In certain embodiments of the invention, the native sequence $P2X_7$ monomeric polypeptides disclosed herein are mature or full-length native sequence polypeptides comprising the full-length amino acids sequence shown in SEQ ID No:1. In certain embodiments the $P2X_7$ receptor may have an amino acid sequence that is modified, for example various of the amino acids in the sequence shown in SEQ ID No:1 may be substituted, deleted, or a residue may be inserted.

"Functional $P2X_7$ receptor" generally refers to a form of the $P2X_7$ receptor having a binding site or cleft for binding to ATP. When bound to ATP, the receptor forms non-selective sodium/calcium channel that converts to a pore-like structure that enables the ingress of calcium ions into the cytosol, one consequence of which may be programmed cell death. In normal homeostasis, expression of functional $P2X_7$ receptors is generally limited to cells that undergo programmed cell death such as thymocytes, dendritic cells, lymphocytes, macrophages and monocytes. There may also be some expression of functional $P2X_7$ receptors on erythrocytes and other cell types.

"Non-functional $P2X_7$ receptor" generally refers to a form of a $P2X_7$ receptor having a conformation whereby the receptor is unable to form an apoptotic pore, but which is still able to operate as a non-selective channel through the maintenance of a single functional ATP binding site located between adjacent monomers. One example arises where one or more of the monomers has a cis isomerisation at Pro210 (according to SEQ ID No:1). The isomerisation may arise from any molecular event that leads to misfolding of the monomer, including for example, mutation of monomer primary sequence or abnormal post translational processing. One consequence of the isomerisation is that the receptor is unable to bind to ATP at one or two ATP binding sites on the trimer and as a consequence not be able to extend the opening of the channel. In the circumstances, the receptor cannot form a pore and this limits the extent to which calcium ions may enter the cytosol. Non-functional $P2X_7$ receptors are expressed on a wide range of epithelial and haematopoietic cancers.

"Cancer associated—$P2X_7$ receptors" are generally $P2X_7$ receptors that are found on cancer cells (including, pre-neoplastic, neoplastic, malignant, benign or metastatic cells), but not on non cancer or normal cells.

"E200 epitope" generally refers to an epitope exposed on a non-functional $P2X_7$ receptor. In humans the sequence is GHNYTTRNILPGLNITC (SEQ ID NO: 2).

"E300 epitope" generally refers to an epitope exposed on a non-functional $P2X_7$ receptor. In humans the sequence is KYYKENNVEKRTLIKVF (SEQ ID NO: 3).

"Composite epitope" generally refers to an epitope that is formed from the juxtaposition of the E200 and E300 epitopes or parts of these epitopes.

"Antibodies" or "immunoglobulins" or "Igs" are gamma globulin proteins that are found in blood, or other bodily fluids of vertebrates that function in the immune system to bind antigen, hence identifying and/or neutralizing foreign objects.

Antibodies are generally a heterotetrameric glycoprotein composed of two identical light (L) chains and two identical heavy (H) chains. Each L chain is linked to a H chain by one covalent disulfide bond. The two H chains are linked to each other by one or more disulfide bonds depending on the H chain isotype. Each H and L chain also has regularly spaced intrachain disulfide bridges.

H and L chains define specific Ig domains. More particularly, each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain (CO at its other end. The $V_L$ is aligned with the $V_H$ and the $C_L$ is aligned with the first constant domain of the heavy chain ($C_H1$).

Antibodies can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2. The L chain from any vertebrate species can be assigned to one of two clearly distinct types, called kappa and lambda, based on the amino acid sequences of their constant domains.

The constant domain includes the Fc portion which comprises the carboxy-terminal portions of both H chains held together by disulfides. The effector functions of antibodies such as ADCC are determined by sequences in the Fc region, which region is also the part recognized by Fc receptors (FcR) found on certain types of cells.

The pairing of a $V_H$ and $V_L$ together forms a "variable region" or "variable domain" including the amino-terminal domains of the heavy or light chain of the antibody. The variable domain of the heavy chain may be referred to as "$V_H$." The variable domain of the light chain may be referred to as "$V_L$." The V domain contains an "antigen binding site" which affects antigen binding and defines specificity of a particular antibody for its particular antigen. V regions span about 110 amino acid residues and consist of relatively invariant stretches called framework regions (FRs) (generally about 4) of 15-30 amino acids separated by shorter regions of extreme variability called "hypervariable regions" (generally about 3) that are each generally 9-12 amino acids long. The FRs largely adopt a β-sheet configuration and the hypervariable regions form loops connecting, and in some cases forming part of, the β-sheet structure.

"Hypervariable region" refers to the regions of an antibody variable domain which are hypervariable in sequence and/or form structurally defined loops. Generally, antibodies comprise six hypervariable regions; three in the $V_H$ (H1, H2, H3), and three in the $V_L$ (L1, L2, L3).

"Framework" or "FR" residues are those variable domain residues other than the hypervariable region residues herein defined.

An "antigen binding site" generally refers to a molecule that includes at least the hypervariable and framework regions that are required for imparting antigen binding function to a V domain. An antigen binding site may be in the form of an antibody or an antibody fragment, (such as a dAb, Fab, Fd, Fv, F(ab')$_2$ or scFv) in a method described herein.

An "intact" or "whole" antibody is one which comprises an antigen-binding site as well as a $C_L$ and at least heavy chain constant domains, $C_H1$, $C_H2$ and $C_H3$. The constant domains may be native sequence constant domains (e.g. human native sequence constant domains) or amino acid sequence variant thereof.

"whole antibody fragments including a variable domain" include Fab, Fab', F(ab)$_2$, and Fv fragments; diabodies; linear antibodies, single-chain antibody molecules; and multispecific antibodies formed from antibody fragments.

The "Fab fragment" consists of an entire L chain along with the variable region domain of the H chain ($V_H$), and the first constant domain of one heavy chain ($C_H1$). Each Fab fragment is monovalent with respect to antigen binding, i.e., it has a single antigen-binding site.

A "Fab' fragment" differs from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group.

A "F(ab)$_2$ fragment" roughly corresponds to two disulfide linked Fab fragments having divalent antigen-binding activity and is still capable of cross-linking antigen.

An "Fv" is the minimum antibody fragment which contains a complete antigen-recognition and binding site. This fragment consists of a dimer of one heavy and one light chain variable region domain in tight, non-covalent association.

In a single-chain Fv (scFv) species, one heavy and one light chain variable domain can be covalently linked by a flexible peptide linker such that the light and heavy chains can associate in a "dimeric" structure analogous to that in a two-chain Fv species. From the folding of these two domains emanate six hypervariable loops (3 loops each from the H and L chain) that contribute the amino acid residues for antigen binding and confer antigen binding specificity to the antibody.

"Single-chain Fv" also abbreviated as "sFv" or "scFv" are antibody fragments that comprise the $V_H$ and $V_L$ antibody domains connected to form a single polypeptide chain. Preferably, the scFv polypeptide further comprises a polypeptide linker between the $V_H$ and $V_L$ domains which enables the scFv to form the desired structure for antigen binding.

A "single variable domain" is half of an Fv (comprising only three CDRs specific for an antigen) that has the ability to recognize and bind antigen, although at a lower affinity than the entire binding site "Diabodies" refers to antibody fragments with two antigen-binding sites, which fragments comprise a heavy-chain variable domain ($V_H$) connected to a light-chain variable domain ($V_L$) in the same polypeptide chain ($V_H$-$V_L$). The small antibody fragments are prepared by constructing sFv fragments (see preceding paragraph) with short linkers (about 5-10 residues) between the $V_H$ and $V_L$ domains such that interchain but not intra-chain pairing of the V domains is achieved, resulting in a bivalent fragment, i.e., fragment having two antigen-binding sites.

Diabodies may be bivalent or bispecific. Bispecific diabodies are heterodimers of two "crossover" sFv fragments in which the $V_H$ and $V_L$ domains of the two antibodies are present on different polypeptide chains. Triabodies and tetrabodies are also generally known in the art.

An "isolated antibody" is one that has been identified and separated and/or recovered from a component of its pre-existing environment. Contaminant components are materials that would interfere with therapeutic uses for the antibody, and may include enzymes, hormones, and other proteinaceous or nonproteinaceous solutes.

A "human antibody" refers to an antibody that possesses an amino acid sequence that corresponds to that of an antibody produced by a human. Human antibodies can be produced using various techniques known in the art, including phage-display libraries. Human antibodies can be prepared by administering the antigen to a transgenic animal that has been modified to produce such antibodies in response to antigenic challenge, but whose endogenous loci have been disabled.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin.

"Monoclonal antibody" refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site or determinant on the antigen. In addition to their specificity, the monoclonal antibodies are advantageous in that they may be synthesized uncontaminated by other antibodies. Monoclonal antibodies may be prepared by the hybridoma methodology. The "monoclonal antibodies" may also be isolated from phage antibody libraries using the techniques.

The term "anti-$P2X_7$ receptor antibody" or "an antibody that binds to $P2X_7$ receptor" refers to an antibody that is capable of binding $P2X_7$ receptor with sufficient affinity such that the antibody is useful as a diagnostic and/or therapeutic agent in targeting $P2X_7$ receptor, typically non-functional $P2X_7$ receptor. Preferably, the extent of binding of an $P2X_7$ receptor antibody to an unrelated protein is less than about 10% of the binding of the antibody to $P2X_7$ receptor as measured, e.g., by a radioimmunoassay (RIA), Enzyme-Linked Immunosorbent Assay (ELISA), Biacore or Flow Cytometry. In certain embodiments, an antibody that binds to $P2X_7$ receptor has a dissociation constant (Kd) of <1 □M, <100 nM, <10 nM, <1 nM, or <0.1 nM. An anti non-functional $P2X_7$ receptor antibody is generally one having some or all of these serological characteristics and that binds to non-functional $P2X_7$ receptors but not to functional $P2X_7$ receptors.

An "affinity matured" antibody is one with one or more alterations in one or more hypervariable region thereof that result in an improvement in the affinity of the antibody for antigen, compared to a parent antibody that does not possess those alteration(s). Preferred affinity matured antibodies will have nanomolar or even picomolar affinities for the target antigen. Affinity matured antibodies are produced by procedures known in the art.

A "blocking" antibody" or an "antagonist" antibody is one that inhibits or reduces biological activity of the antigen it binds. Preferred blocking antibodies or antagonist antibodies substantially or completely inhibit the biological activity of the antigen.

An "agonist antibody", as used herein, is an antibody, which mimics at least one of the functional activities of a polypeptide of interest.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity, which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

"Epitope" generally refers to that part of an antigen that is bound by the antigen binding site of an antibody. An epitope may be "linear" in the sense that the hypervariable loops of the antibody CDRs that form the antigen binding site bind to a sequence of amino acids as in a primary protein structure. In certain embodiments, the epitope is a "conformational epitope" i.e. one in which the hypervariable loops of the CDRs bind to residues as they are presented in the tertiary or quaternary protein structure.

'Treatment' generally refers to both therapeutic treatment and prophylactic or preventative measures.

Subjects requiring treatment include those already having a benign, pre-cancerous, or non-metastatic tumor as well as those in which the occurrence or recurrence of cancer is to be prevented.

The objective or outcome of treatment may be to reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder.

Efficacy of treatment can be measured by assessing the duration of survival, time to disease progression, the response rates (RR), duration of response, and/or quality of life.

In one embodiment, the method is particularly useful for delaying disease progression.

In one embodiment, the method is particularly useful for extending survival of the human, including overall survival as well as progression free survival.

In one embodiment, the method is particularly useful for providing a complete response to therapy whereby all signs of cancer in response to treatment have disappeared. This does not always mean the cancer has been cured.

In one embodiment, the method is particularly useful for providing a partial response to therapy whereby there has been a decrease in the size of one or more tumors or lesions, or in the extent of cancer in the body, in response to treatment.

"Pre-cancerous" or "pre-neoplasia" generally refers to a condition or a growth that typically precedes or develops into a cancer. A "pre-cancerous" growth may have cells that are characterized by abnormal cell cycle regulation, proliferation, or differentiation, which can be determined by markers of cell cycle.

In one embodiment, the cancer is pre-cancerous or pre-neoplastic.

In one embodiment, the cancer is a secondary cancer or metastases. The secondary cancer may be located in any organ or tissue, and particularly those organs or tissues having relatively higher hemodynamic pressures, such as lung, liver, kidney, pancreas, bowel and brain.

Other examples of cancer include blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, leukemia or lymphoid malignancies, lung cancer including small-cell lung cancer (SGLG), non-small cell lung cancer (NSGLG), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, as well as head and neck cancer.

"A condition or symptom associated" [with the cancer] may be any pathology that arises as a consequence of, preceding, or proceeding from the cancer. For example, where the cancer is a skin cancer, the condition or relevant symptom may be microbial infection. Where the cancer is a secondary tumor, the condition or symptom may relate to organ dysfunction of the relevant organ having tumor metastases. In one embodiment, the methods of treatment described herein are for the minimisation or treatment of a condition or symptom in an individual that is associated with a cancer in the individual.

A "non self" molecule, such as a "non self" antigen binding site, or "non self" antibody generally refers to a molecule that has been produced outside of, or exogenous to, a body in which the molecule is to be provided, for example, for treatment. As an example, synthetic or recombinant molecules are "non self". Further, a molecule that is generated in one individual and administered to another individual for treatment is "non self". "Non self" antigen binding sites and antibodies may be used in accordance with the invention for adoptive transfer of immunity, for example, as occurs in antibody infusion. In contrast, a molecule that is generated inside an individual that is to be treated with that molecule, is generally a "self" or "endogenous" molecule. One example of a "self" molecule is an antigen binding site or antibody that is generated, or arises from an adaptive immune response to immunogen.

"level of non self antigen binding sites in circulation" in the individual generally refers to the concentration of antigen binding site in a body fluid, preferably peripheral blood.

A "substantially undetectable level of non self antigen binding sites in circulation" generally refers to a concentration of exogenous antigen binding sites (i.e. those that have been administered by adoptive transfer) that is at least half of the concentration of the antigen binding sites in circulation at the time of administration of the antigen binding sites, preferably 25%, or 10%, or 5% or 1% of said concentration, or otherwise less than 0.001 mg/kg of the individual. The phrase may also refer to a circumstance where antigen binding sites that have been given for the purpose of cancer immunotherapy cannot be detected at all.

A cancer that is "substantially undetectable" generally refers to a circumstance where therapy has depleted the size, volume or other physical measure of a cancer so that using relevant standard detection techniques such as in vivo imaging, the cancer, as a consequence of the therapy, is not clearly detectable. The phrase also refers to the circumstance where the cancer cannot be detected at all.

"forming an immune response" generally refers to invoking or inducing antigen specific immunity via the adaptive immune system. As is generally understood in the art, induction of antigen specific immunity is distinguished from adoptive transfer of immunity, standard cancer immunotherapy by administration of exogenous or non self antibody being one example of the latter.

Individuals Selected for Treatment

Generally, the individuals selected for treatment according to a method described above are those who have received, or who are continuing to receive antibody immunotherapy, for treatment of cancer. Antibody immunotherapy generally means the administration of exogenous, (otherwise known as or "non self") antibodies to an individual requiring treatment, as in the case of adoptive transfer of antibody. For example, the individual may have received any one of the therapeutic antibodies that have received regulatory approval for indications related to oncology. Avastin, Herceptin, Rituxan are examples. Typically the individual has received or is continuing to receive an anti $P2X_7$ receptor antibody.

In one embodiment, the individual may have received immunotherapy leading to undetectable tumour mass and no longer has detectable circulating exogenous antibody at the time of immunisation.

Figure 2:
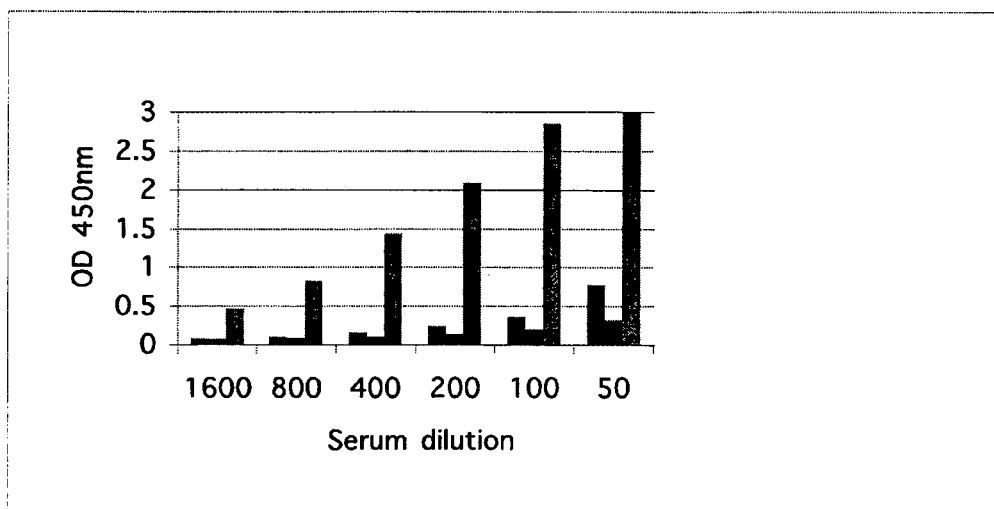

Further, the individual selected for treatment according to a method described above may or may not have detectable cancer at the time of treatment. Where the individual does not have detectable cancer, a primary or secondary humoral response is more easily detected because, with the cancer being present in substantially undetected amount, there is very little non-functional $P2X_7$ receptor available to remove IgM or IgG from body fluid. This point is demonstrated in FIGS. 1 and 2.

The purpose of the treatment according to the above described methods is to at least minimise the progression of cancer by induction or formation of an immune response in the individual to a non-functional $P2X_7$ receptor. Therefore, the individual selected for treatment must be capable of generating an immune response sufficient for meeting this purpose. Generally the desired immune response includes a capacity to produce either or both of circulating IgM and IgG when the individual is challenged by cancer, as in recurrence of cancer. In one embodiment, the presence of an immune response to non-functional $P2X_7$ receptor is measured or assessed when the individual does not have detectable cancer. In these circumstances it is believed that the absence of an anti-$P2X_7$ receptor antibody-absorbing mass in the form of tumour increases the likelihood of there being a higher systemic titre of anti-$P2X_7$ receptor antibody.

Individuals having a capacity to generate the immune response described herein may be selected or screened by a variety of methods well known in the art for detection of immunodeficiency. Typically, the individual selected for treatment will be one having at least one white blood cell component count within normal parameters. For example, an individual for inclusion is generally one having a white blood cell count of between 4.0 to $11.0 \times 10^9$/L, or a lymphocyte count of between 1.0 to $4.4 \times 10^9$/L. Neutrophil count may be between $1.9$-$7.8 \times 10^9$/L; monocyte count between $0.2$-$1.0 \times 10^9$/L, eosinophil less than about $5.0 \times 10^9$/L and basophil less than about $0.2 \times 10^9$/L.

It will be understood that in certain embodiments the cell count for any one of these blood cell components may fall outside these stated ranges, particularly in circumstances where the individual has a form of blood cancer, for example CML, CLL etc.

Generally an important factor is the lymphocyte count and/or monocyte count. In more detail, where either or both of these counts are significantly below the stated ranges for these components, the individual may be less likely to respond to administration of the immunogen.

In another embodiment, the selection of an individual for therapy may involve a screening step for screening whether the individual is homozygous for non-functional $P2X_7$ receptor expression. In more detail, a small percentage of the Caucasian population is understood to have non-functional $P2X_7$ receptor expression on non cancer cells such as certain thymocytes, dendritic cells, lymphocytes, macrophages, monocytes and erythrocytes. Other individuals may be heterozygotic for this expression. In one embodiment, individuals who are homozygotic for non-functional $P2X_7$ receptor expression are screened for and excluded from treatment, in which case individuals included for treatment do not express non-functional $P2X_7$ receptor on non cancer cells, or otherwise have heterozygotic expression.

Where the individual is continuing to receive antibody immunotherapy, in one embodiment the antibody immunotherapy is allowed to continue to the desired clinical endpoint. Typically the desired clinical endpoint is a reduction of cancer to substantially undetectable levels. During, or at the completion of immunotherapy, the capacity of the individual to form, or generate an immune response to a $P2X_7$ receptor is then assessed. Where the assessment reveals that the individual is likely to benefit from immunisation with $P2X_7$ immunogen, the individual is then administered with immunogen.

In a preferred form of the invention, the level of non self or exogenous antigen binding sites in circulation in the individual arising from antibody immunotherapy is substantially undetectable at the time that the immune response is formed in the individual. Importantly, where the non self antigen binding site binds to non functional $P2X_7$ receptor or cancer-associated $P2X_7$ receptor, a key finding of the inventor is that efficacy of antibody treatment, particularly when cancer cells are in very low copy number, or otherwise substantially undetectable, decreases at higher circulating concentrations of antigen binding sites. This is believed to be a function of the low copy number of $P2X_7$ receptors on cancer cells relative to the high concentration of antigen binding sites that arise in standard antibody immunotherapy. Specifically, in the Examples herein, the inventor has found that as the circulatory level of antigen specific binding sites increase, and the number of cancer cells decrease, there is a much higher likelihood of crowding of the $P2X_7$ receptor by antigen binding sites that block antigen specific binding of the receptor. This blockage increases the likelihood that the intended cytotoxic, apoptotic or other effects of antigen specific binding by an antigen binding site will not be possible. One can determine the level of exogenous antigen binding sites in circulation by any standard serological technique capable of detecting antibody in fluid, one preferred example being ELISA using an antibody to capture antigen binding sites.

Further to the above, while not wanting to be bound by hypothesis, the inventors consider that administration of immunisation at a time where infded antibody is present increases the risk that the infused antibody could bind to the immunogen, resulting in immune complex formation and clearance, thereby avoiding antigen presentation and induction of antigen specific immunity. Therefore, in certain embodiments it is particularly useful to wait until the level of non self or exogenous antigen binding sites have been cleared from circulation before induction of the antigen specific immune response to immunogen.

In embodiments where the infused antibody cannot bind the immunogen (i.e. because the antibody is not specific for the immunogen, for example where the antibody binds to a biomarker that is unrelated to the immunogen) the immunisation with immunogen may occur when there is detectable infused antibody, or before antibody infusion occurs.

Antigen Binding Sites and Administration

An individual to be treated in accordance with the methods described herein may be one who has received, or is to receive any one of the therapeutic antibodies indicated for oncology. Preferably, the individual has received or is continuing to receive an anti $P2X_7$ receptor antibody.

Typically the antigen binding site is one that discriminates between functional and non-functional $P2X_7$ receptors, so as to bind to non-functional receptors, but not to functional receptors. Examples of these antigen binding sites are those that bind to the E200 epitope, E300 epitope or composite epitope as for example in PCT/AU2002/000061, PCT/AU2002/001204, PCT/AU2007/001540, PCT/AU2007/001541, PCT/AU2008/001364, PCT/AU2008/001365, PCT/AU2009/000869 and PCT/AU2010/001070, all of which are incorporated by reference.

Regardless of specificity, (i.e. $P2X_7$ receptor specific or otherwise), the antigen binding site may take the form of a whole antibody, or a whole antibody fragment such as a Fab, a Fab', a F(ab')$_2$, and Fv, a single chain Fv, or a single variable domain.

The antigen binding site may be syngeneic, allogeneic or xenogeneic.

Typically the antigen binding site is non self or exogenous meaning that it has been found or isolated outside of the individual who is treated according to the methods of the invention.

The antigen binding site may be affinity matured.

The antigen binding site may have multiple specificities or valencies.

The antigen binding site may be adapted so as to be suited to administration by a selected method.

The antibody may be a whole antibody of any isotype. The antibody may be one obtained from monoclonal or polyclonal antisera. The antibody may be produced by hybridoma, or by recombinant expression, or may be obtained from serum for example as obtainable from a mammal, particularly a human or mouse. The antibody may also be obtained from an avian.

The antibody may be chimeric, i.e. one containing human variable domains and non human constant domains. Alternatively, it may be humanized, i.e one formed by grafting non human CDRs onto a human antibody framework. Still further, the antibody may be fully human.

The antibody may be modified with respect to effector function, so as to enhance, e.g., the effectiveness of the antibody in treating cancer.

Where the antibody is an antibody fragment, the antibody fragment is selected from the group consisting of a dAb, Fab, Fd, Fv, F(ab')$_2$, scFv and CDR.

Dosage amount, dosage frequency, routes of administration etc are described in detail below.

Methods of preparing and administering antibodies to a subject in need thereof are well known to, or are readily determined by those skilled in the art. The route of administration may be, for example, oral, parenteral (e.g. intravenous, intraarterial, intraperitoneal, intramuscular, subcutaneous, intradermal, rectal or vaginal), by inhalation or topical. One form for administration would be a solution for injection, in particular for intravenous or intraarterial injection or drip, comprising a buffer (e.g. acetate, phosphate or citrate buffer), a surfactant (e.g. polysorbate), optionally a stabilizer agent (e.g. human albumin). In other methods antibodies can be delivered directly to the site of disease thereby increasing the exposure of the diseased cell or tissue to the antibody.

Preparations for parenteral administration includes sterile aqueous (aqueous carriers include water, alcoholic/aqueous solutions, emulsions or suspensions, including saline and buffered media) or non-aqueous (non-aqueous solvents are propylene glycol, polyethylene glycol, vegetable oils such as olive oil, and injectable organic esters such as ethyl oleate) solutions, suspensions, and emulsions. Pharmaceutically acceptable carriers include 0.01-0.1M and preferably 0.05M phosphate buffer or 0.9% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions, in such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences, Mack Publishing Co., 16th ed. (1980).

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., antigen binding site) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying, freeze-drying and spray drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit. Such articles of manufacture will preferably have labels or package inserts indicating that the associated compositions are useful for treating a subject suffering from, or predisposed to disorders.

Effective doses of the compositions of the present invention, for treatment of disorders, as described herein, vary depending upon many different factors, including means of administration, target site, physiological state of the patient, whether the patient is human or an animal, other medications administered, and whether treatment is prophylactic or therapeutic. Treatment dosages may be titrated using routine methods known to those of skill in the art to optimize safety and efficacy.

For treatment of certain disorders with an antibody, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more antigen binding sites with different binding specificities are administered simultaneously, in which case the dosage of each antigen binding site administered falls within the ranges indicated.

The antibody for binding to a non-functional $P2X_7$ receptor expressed on a cell can be administered on multiple occasions. Intervals between single dosages can be weekly, monthly or yearly. Intervals can also be irregular as indicated by measuring blood levels of target polypeptide or target molecule in the patient. In some methods, dosage is adjusted to achieve a plasma polypeptide concentration of 1-1000 ug/mL and in some methods 25-300 ug/mL. Alternatively, the antibody can be administered as a sustained release formulation, in which case less frequent administration is required. Dosage and frequency vary depending on the half-life of the antibody in the patient. The half-life of an antibody can also be prolonged via fusion to a stable polypeptide or moiety, e.g., albumin or PEG. In general, humanized antibodies show the longest half-life, followed by chimeric antibodies and nonhuman antibodies. In one embodiment, the antibody can be administered in unconjugated form. In another embodiment the antibody can be administered multiple times in conjugated form. In certain therapeutic applications, a relatively high dosage (e.g., up to 400 mg/kg of anti $P2X_7$ binding molecule, e.g., antibody per dose), at relatively short intervals is sometimes required until progression of the disease is reduced or terminated, and preferably until the patient shows partial or complete amelioration of symptoms of disease. The amounts can be several logs lower (i.e. 2 to 3 logs lower) where the antibody is conjugated to a radioisotope or cytotoxic drug.

Therapeutic agents can be administered by parenteral, topical, intravenous, oral, subcutaneous, intraarterial, intracranial, intraperitoneal, intranasal or intramuscular means for prophylactic and/or therapeutic treatment, in some methods, agents are injected directly into a particular tissue where non-functional $P2X_7$ receptor cells have accumulated, for example intracranial injection. Intramuscular injection or intravenous infusion are preferred for administration of antibody.

An antibody can optionally be administered in combination with other agents that are effective in treating the disorder or condition in need of treatment (e.g., prophylactic or therapeutic). Examples are agents commonly used for chemotherapy or radiotherapy in oncology. Additionally or alternatively, the antibody or agent may be administered before, during or after surgical intervention for resection or removal of tumor or tissue.

Immunogens and Forming an Immune Response

The methods of the invention described herein require the formation of an immune response in an individual to be treated to a P2X$_7$ receptor, especially a non-functional P2X$_7$ receptor. Generally the immunogen, which is used for the purpose, is one which elicits an immune response to non-functional P2X$_7$ but not to functional P2X$_7$ receptors.

The immunogen may include or consist of a peptide including a sequence of a P2X$_7$ receptor. The peptide may contain at least one sequence that is capable of being presented on a major histocompatibility complex class II molecule or, that is capable of interacting with a B-cell receptor or a B-cell membrane bound-immunoglobulin. Typically the peptide includes a sequence of a human P2X$_7$ receptor or fragment thereof.

A range of peptide immunogens are known and discussed in PCT/AU2002/000061, PCT/AU2002/000061, PCT/AU2008/001364 and PCT/AU2009/000869, the contents of which are incorporated in entirety.

Exemplary peptides immunogens within these specifications, which include epitopes for generating an immune response to a non-functional P2X$_7$ receptor are described below.

| PCT application | Peptide immunogen sequence |
|---|---|
| PCT/AU2002/000061, PCT/AU2002/000061 | GHNYTTRNILPGLNITC (SEQ ID NO: 2) |
| PCT/AU2008/001364 | KYYKENNVEKRTLIKVF (SEQ ID NO: 3) |
| PCT/AU2009/000869 | GHNYTTRNILPGAGAKYYKENNVEK (SEQ ID NO: 4) |

It will be understood that these are merely examples of possible immunogens useful for forming an immune response according to the methods of the invention described herein. Further, the invention includes the use of other peptides as described in these applications useful for forming an immune response to non-functional P2X$_7$ receptors.

Typically the immunisation regime involves 2 or more immunisations. In a first immunisation, the objective may be to develop an IgM response to immunisation. A second immunisation may be to develop an IgG response. Further immunisations may be to boost the IgG response, as discussed further below.

Where the immunogen is a peptide, the peptide may be provided in an amount of about 0.1 to 1 mg per administration, preferably about 0.25 to 0.75 mg, preferably about 0.5 mg.

A further administration of about 0.3 mg peptide may be applied as a boost.

In one embodiment, a first immunisation is performed when the circulating level of antigen binding sites that had been administered for antibody immunotherapy is substantially undetectable. In other words, circulating antibody to the relevant cancer biomarker cannot be detected in peripheral blood. The level of IgM production is then monitored over the following weeks. At about 4 to 5 weeks after first immunisation, the level of IgM antibody is likely to have decreased to negligible circulating levels. At this point, a second immunisation is then performed and the level of IgG production is monitored over the following weeks.

After boosting, the level of antibody produced may be 0.1-25 mg/kg, for example from 0.1 to 10 mg/kg, preferably 5 mg/kg, or from 10 to 25 mg/kg, preferably 15 mg/kg and more than 10 mg/kg. Whether this amount is detected in circulation will depend on whether there is existing tumour mass. Where there is existing tumour mass capable of binding to antibody formed by the humoral response, the level of antibody detected in circulation may be at the lower end of this range, or indeed outside the lower end of the range (i.e. less than 0.1 mg/kg), or otherwise substantially undetectable. Where there is no detectable tumour mass, the level of antibody formed from the humoral response may be at the higher end of this range, although in certain embodiments, in these circumstances, an amount of about 5 mg/kg antibody may be sufficient. Further testing of immunity over the following months/years may be performed and boosting immunisations may be provided as required.

The degree or number of boosts may depend on the patient status and response. Where scans or lack of free circulating antibody are indicative of extant tumour burden, then boosts may be performed monthly, ideally to ensure sufficient reaction of the immune system. Where the free levels of antibody in serum rise, the boosts may then be eased off and perhaps applied 6-12 monthly subject to clinical observation.

As discussed above, the immune response may target a biomarker that is different to the biomarker that has been targeted by antibody immunotherapy. For example, anti CD20 antibody may be used for antibody immunotherapy and a non-functional P2X$_7$ immunogen used for generating an immune response.

In another embodiment, a single biomarker is targeted by antibody immunotherapy and immunisation. For example, a monoclonal antibody directed to one epitope on a P2X$_7$ receptor (such as the E300 epitope) may be used for antibody immunotherapy, and an immunogen for forming an immune response that targets a different epitope (such as the E200 epitope) on P2X$_7$ may be used for immunisation.

A peptide immunogen for use in a method of the invention herein may have a length of 6, 7, 8, 9, 10, 11, 12, 13, 14, 15, 16, 17, 18, 19, 20, 21, 22, 23, 24, 25 or 26 residues.

In one embodiment, the immunogen for forming an immune response according to a method of the invention is a peptide having a sequence of a P2X$_7$ receptor that may or may not have Pro210 in cis conformation.

The immunogen may be in the form of a P2X$_7$ extracellular domain or any one or more of the P2X$_7$ isoforms. The immunogen may be provided for administration in a soluble form or associated with a solid phase such as a cell membrane, bead, or other surface.

Methods for screening peptides that can be used as an immunogen to form an immune response according to the methods of the invention herein are disclosed herein. One example includes the use of erythrocytes in a rosetting assay. In this assay an antibody that binds to functional receptors is used as a positive control in which rossettes are observed. A test antibody is determined not to bind to functional receptors if it fails to form rossettes. It is determined to bind to non-functional receptors if it is observed to bind to a non-functional receptor-expressing cell line, including those discussed herein.

The peptides of the invention can be made by any number of techniques known in the art including solid phase synthesis and recombinant DNA technology.

As is known in the art, a carrier is a substance that may be conjugated to a peptide epitope thereby enhancing immunogenicity. Some carriers do this by binding to multiple peptides so as to provide an antigen of increased molecular weight to the host in which the immune response is to be developed.

Preferred carriers include bacterial toxins or toxoids. Other suitable carriers include the *N. meningitides* outer membrane protein, albumin such as bovine serum albumin, synthetic peptides, heat shock proteins, KLH, Pertussis proteins, protein D from *H. influenza* and toxin A, B or C from *C. difficile*.

When the carrier is a bacterial toxin or toxoid, diphtheria or tetanus toxoids are preferred.

Preferably the carrier contains functional groups that can react with the peptide of the invention, or may be modified to be capable of reacting with the peptide.

The immunogen may be administered subcutaneously, intradermally and/or intramuscularly.

Adjuvants

In a preferred form, the composition for forming an immune response to a $P2X_7$ receptor for use in the methods of the invention described herein includes an adjuvant or compound for potentiating an immune response.

A large number of adjuvants are known; See also Allison (1998, Dev. Biol. Stand., 92:3-11; incorporated herein by reference), Unkeless et al. (1998, Annu. Rev. Immunol., 6:251-281), and Phillips et al. (1992, Vaccine, 10:151-158). Exemplary adjuvants that can be utilized in accordance with the invention include, but are not limited to, cytokines, aluminium salts (e.g., aluminium hydroxide, aluminium phosphate, etc.; Baylor et al., Vaccine, 20:S18, 2002), gel-type adjuvants (e.g., calcium phosphate, etc.); microbial adjuvants (e.g., immunomodulatory DNA sequences that include CpG motifs; endotoxins such as monophosphoryl lipid A (Ribi et al., 1986, Immunology and Immunopharmacology of bacterial endotoxins, Plenum Publ. Corp., NY, p407, 1986); exotoxins such as cholera toxin, *E. coli* heat labile toxin, and pertussis toxin; muramyl dipeptide, etc.); oil-emulsion and emulsifier-based adjuvants (e.g., Freund's Adjuvant, MF59 [Novartis], SAF, etc.); particulate adjuvants (e.g., liposomes, biodegradable microspheres, etc.); synthetic adjuvants (e.g., nonionic block copolymers, muramyl peptide analogues, polyphosphazene, synthetic polynucleotides, etc.); and/or combinations thereof. Other exemplary adjuvants include some polymers (e.g., polyphosphazenes; described in U.S. Pat. No. 5,500,161), Q57, saponins (e.g., QS21, Ghochikyan et al., Vaccine, 24:2275, 2006), squalene, tetrachlorodecaoxide, CPG 7909 (Cooper et al., Vaccine, 22:3136, 2004), poly[di(carboxylatophenoxy)phosphazene] (PCCP; Payne et al., Vaccine, 16:92, 1998), interferon-γ (Cao et al., Vaccine, 10:238, 1992), block copolymer P1205 (CRL1005; Katz et al., Vaccine, 18:2177, 2000), interleukin-2 (IL-2; Mbwuike et al., Vaccine, 8:347, 1990), polymethyl methacrylate (PMMA; Kreuter et al., J. Pharm. ScL, 70:367, 1981), etc.

In one embodiment, a peptide immunogen containing a sequence of a $P2X_7$ receptor is provided on the surface of a bacteriophage for immunisation of an individual according to a method of the invention described herein.

Cancers and Conditions Associated Therewith

Pre-neoplastic, neoplastic and metastatic diseases are particular examples to which the methods of the invention may be applied. Broad examples include breast tumors, colorectal tumors, adenocarcinomas, mesothelioma, bladder tumors, prostate tumors, germ cell tumor, hepatoma/cholongio, carcinoma, neuroendocrine tumors, pituitary neoplasm, small round cell tumor, squamous cell cancer, melanoma, atypical fibroxanthoma, seminomas, nonseminomas, stromal leydig cell tumors, Sertoli cell tumors, skin tumors, kidney tumors, testicular tumors, brain tumors, ovarian tumors, stomach tumors, oral tumors, bladder tumors, bone tumors, cervical tumors, esophageal tumors, laryngeal tumors, liver tumors, lung tumors, vaginal tumors and Wilm's tumor.

Examples of particular cancers include but are not limited to adenocarcinoma, adenoma, adenofibroma, adenolymphoma, adontoma, AIDS related cancers, acoustic neuroma, acute lymphocytic leukemia, acute myeloid leukemia, adenocystic carcinoma, adrenocortical cancer, agnogenic myeloid metaplasia, alopecia, alveolar soft-part sarcoma, ameloblastoma, angiokeratoma, angiolymphoid hyperplasia with eosinophilia, angioma sclerosing, angiomatosis, apudoma, anal cancer, angiosarcoma, aplastic anaemia, astrocytoma, ataxia-telangiectasia, basal cell carcinoma (skin), bladder cancer, bone cancers, bowel cancer, brain stem glioma, brain and CNS tumors, breast cancer, branchioma, CNS tumors, carcinoid tumors, cervical cancer, childhood brain tumors, childhood cancer, childhood leukemia, childhood soft tissue sarcoma, chondrosarcoma, choriocarcinoma, chronic lymphocytic leukemia, chronic myeloid leukemia, colorectal cancers, cutaneous T-cell lymphoma, carcinoma (e.g. Walker, basal cell, basosquamous, Brown-Pearce, ductal, Ehrlich tumor, Krebs 2, Merkel cell, mucinous, non-small cell lung, oat cell, papillary, scirrhous, bronchiolar, bronchogenic, squamous cell, and transitional cell), carcinosarcoma, cervical dysplasia, cystosarcoma phyllodies, cementoma, chordoma, choristoma, chondrosarcoma, chondroblastoma, craniopharyngioma, cholangioma, cholesteatoma, cylindroma, cystadenocarcinoma, cystadenoma, dermatofibrosarcoma-protuberans, desmoplastic-small-round-cell-tumor, ductal carcinoma, dysgerminoam, endocrine cancers, endometrial cancer, ependymoma, esophageal cancer, Ewing's sarcoma, extra-hepatic bile duct cancer, eye cancer, eye: melanoma, retinoblastoma, fallopian tube cancer, fanconi anaemia, fibroma, fibrosarcoma, gall bladder cancer, gastric cancer, gastrointestinal cancers, gastrointestinal-carcinoid-tumor, genitourinary cancers, germ cell tumors, gestationaltrophoblastic-disease, glioma, gynaecological cancers, giant cell tumors, ganglioneuroma, glioma, glomangioma, granulosa cell tumor, gynandroblastoma, haematological malignancies, hairy cell leukemia, head and neck cancer, hepatocellular cancer, hereditary breast cancer, histiocytosis, Hodgkin's disease, human papillomavirus, hydatidiform mole, hypercalcemia, hypopharynx cancer, hamartoma, hemangioendothelioma, hemangioma, hemangiopericytoma, hemangiosarcoma, hemangiosarcoma, histiocytic disorders, histiocytosis malignant, histiocytoma, hepatoma, hidradenoma, hondrosarcoma, immunoproliferative small, opoma, ontraocular melanoma, islet cell cancer, Kaposi's sarcoma, kidney cancer, langerhan's cell-histiocytosis, laryngeal cancer, leiomyosarcoma, leukemia, li-fraumeni syndrome, lip cancer, liposarcoma, liver cancer, lung cancer, lymphedema, lymphoma, Hodgkin's lymphoma, non-Hodgkin's lymphoma, leigomyosarcoma, leukemia (e.g. b-cell, mixed cell, null-cell, t-cell, t-cell chronic, htiv-ii-associated, lymphangiosarcoma, lymphocytic acute, lymphocytic chronic, mast-cell and myeloid), leukosarcoma, leydig cell tumor, liposarcoma, leiomyoma, leiomyosarcoma, lymphangioma, lymphangiocytoma, lymphagioma, lymphagiomyoma, lymphangiosarcoma, male breast cancer, malignant-rhabdoid-tumor-of-kidney, medulloblastoma, melanoma, Merkel cell cancer, mesothelioma, metastatic cancer, mouth cancer, multiple endocrine neoplasia, mycosis fungoides, myelodysplastic syndromes, myeloma, myeloproliferative disorders, malignant carcinoid syndrome carcinoid heart disease, medulloblastoma, meningioma, melanoma, mesenchymoma, mesonephroma, mesothelioma, myoblastoma, myoma, myosarcoma, myxoma, myxosarcoma, nasal cancer, nasopharyngeal cancer, nephroblastoma, neuroblastoma, neurofibromatosis, Nijmegen breakage syndrome, non-melanoma skin cancer, non-small-cell-lung-cancer-(nscic), neurilemmoma, neuroblastoma, neuroepithelioma, neurofibromatosis, neurofibroma, neuroma, neoplasms (e.g. bone, breast, digestive system, colorectal, liver), ocular cancers, oesophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal-tumors, pituitary cancer, polycythemia vera, prostate cancer, osteoma, osteosarcoma, ovarian carcinoma, papilloma, paraganglioma, paraganglioma nonchromaffin, pinealoma, plasmacytoma, protooncogene, rare-cancers-and-associated-disorders, renal cell carcinoma, retinoblastoma, rhabdomyosarcoma, Rothmund-Thomson syndrome, reticuloendotheliosis, rhabdomyoma, salivary gland cancer, sarcoma, schwannoma, Sezary syndrome, skin cancer, small cell lung cancer (scic), small intestine cancer, soft tissue sarcoma, spinal cord tumors, squamous-cell-carcinoma-(skin), stomach cancer, synovial sarcoma, sarcoma (e.g. Ewing's experimental, Kaposi's and mast-cell sarcomas), Sertoli cell tumor, synovioma, testicular cancer, thymus cancer, thyroid cancer, transitional-cell-cancer-(bladder), transitional-cell-cancer-(renal-pelvis-/- ureter), trophoblastic cancer, teratoma, theca cell tumor, thymoma, trophoblastic tumor, urethral cancer, urinary system cancer, uroplakins, uterine sarcoma, uterus cancer, vaginal cancer, vulva cancer, Waldenstrom's-macroglobulinemia and Wilms' tumor.

Kits

In another embodiment there is provided a kit or article of manufacture including:

an antigen binding site in the form of an immunoglobulin variable domain, antibody, dAb, Fab, Fd, Fv, F(ab')$_2$, scFv or CDR reactive with a P2X$_7$ receptor, preferably a non-functional P2X$_7$ receptor;

an immunogen for generating an immune response to a non-functional P2X$_7$ receptor; and a label or package insert with instructions for use in a method described herein.

EXAMPLES

Example 1

Induction of Immune Response in CML Patient

Material and Methods

Peptide

Peptide immunogen was synthesised to high purity in the form GHNYTTRNILPGLNITC (SEQ ID NO:2) to which was added the cross-linker maleimidocaproyl-N-hydroxysuccinimide (MCS) at the C-terminal Cys residue. The peptide was cross-linked to a carrier protein Keyhole Limpet Hemocyanin (KLH) such that the average percentage of peptide to total peptide-protein conjugate was 40%. This peptide or the alternative peptide GHNYTTRNILPGA-GAKYYKENNVEKC (SEQ ID NO:5) similarly conjugated to KLH constituted selective epitope targets, primary and compound respectively that enabled differentiation of the nfP2X.sub.7 receptors to be made from native receptors.

Adjuvant

Imject Alum, an approved adjuvant commonly used in human immunisations, consisting of an aqueous formulation of aluminium hydroxide and magnesium hydroxide plus inactive stabilisers in a gel, was used. The peptide-protein conjugate was added at a concentration of 2.5 mg/mL conjugate (1 mg/mL peptide) dropwise with thorough mixing in the adjuvant in an amount equal to 0.5 mL conjugate to 0.75 mL adjuvant containing 0.5 mg of target peptide epitope.

Immunisation

The immunisation schedule consisted of a primary inoculation (two injections subcutaneously and two injections intramuscularly) of a total of 0.5 mg peptide followed a month later with a boost applied the same way with 0.3 mg peptide. Serum samples were collected immediately prior to and a week post injections. Inoculation is ideally administered no less than a month after the final infusion of anti-nfP2X$_7$ antibody to ensure no sequestration of the immunogen by residual specific anti-nfP2X$_7$ antibody infusate.

ELISA

Specific anti-nfP2X$_7$ antibody responses were measured by ELISA. In brief, the ELISA plate was coated with specific target peptide epitope, either naked or conjugated to a carrier other than the one against which the antibody response was generated, over which patient serum is added in a descending concentration. After washing, an appropriate secondary anti-human antibody (anti-IgM or anti-IgG types) is applied to detect and determine the concentration of specific human anti-nfP2X$_7$ antibody present in the patient serum in the form of IgM or IgG.

Following the inoculation, no IgG is detectable but a small amount of IgM is detected. Following the boost, the IgM concentration has returned to a baseline of zero while IgG is produced at higher concentration than the original IgM provided no nfP2X$_7$ receptor sink is present on extant tumor. In the absence of such a sink in patients for which the original tumor has been cleared by anti-nfP2X$_7$ immunotherapy or alternate therapies, a clear population of specific endogenous anti-nfP2X$_7$ antibody is detected in the serum, of order 5 mg/kg.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method for minimising the progression of cancer in an individual who has received a non-self antibody or antigen-binding fragment thereof for treatment of the cancer, the method including the step of:
forming an immune response to a $P2X_7$ receptor in an individual who has received a non self antibody or antigen binding fragment thereof for treatment of the cancer by administering to the individual a peptide comprising the amino acid sequence GHNYTTRNIL-PGLNITC (SEQ ID NO:5);
wherein cancer in the individual has been reduced in size, mass or other physical measure by the administration of the non self antibody or antigen binding fragment thereof;
thereby minimising the progression of cancer in the individual.

2. The method of claim 1 wherein the individual does not have detectable non-self antibody or antigen-binding fragment thereof in circulation at the time of administering the peptide.

3. The method of claim 1 wherein the reduction in size, mass or other physical measure results in the individual not having detectable cancer.

4. The method of claim 1 wherein the individual has developed an immune response to the non-self antibody or antigen-binding fragment thereof.

5. The method of claim 1 wherein the non-self antibody or antigen-binding fragment thereof binds to non-functional $P2X_7$ receptor, but not to functional $P2X_7$ receptor.

6. The method of claim 1 wherein the non-self antibody or antigen-binding fragment thereof received by the individual for treatment of the cancer does not bind to a $P2X_7$ receptor, or a fragment of a $P2X_7$ receptor.

7. The method of claim 1 wherein the peptide is provided in an initial administration to the individual, thereby forming a response that includes IgM production in the individual.

8. The method of claim 1 wherein the peptide is provided in an initial administration to the individual, thereby forming a response that includes IgM production, and at a later time, in a further administration to the initial administration, thereby forming a response that includes IgG production.

9. A process for forming a humoral immune response to cancer-associated $P2X_7$ receptors in an individual who has received an anti-cancer antigen antibody for therapy of cancer, including the steps of:
forming an immune response in the individual by administering to the individual a peptide comprising the amino acid sequence GHNYTTRNILPGLNITC (SEQ ID NO:5);
wherein the immune response is formed in the individual at a time where anti-cancer antigen antibody administered for treatment of cancer is at a level or concentration that is substantially undetectable in the individual; and/or
the humoral immune response to cancer-associated $P2X_7$ receptors is formed according to an immunisation schedule whereby the amount of antibody formed in the individual to cancer-associated $P2X_7$ receptor is about 0.1 to 25 mg/kg individual.

* * * * *

UNITED STATES PATENT AND TRADEMARK OFFICE
CERTIFICATE OF CORRECTION

PATENT NO. : 9,566,318 B2
APPLICATION NO. : 14/129240
DATED : February 14, 2017
INVENTOR(S) : Julian Alexander Barden et al.

Page 1 of 1

It is certified that error appears in the above-identified patent and that said Letters Patent is hereby corrected as shown below:

In the Claims

In Claim 1, at Column 27, Line 26, delete the text "SEQ ID NO:5" and replace it with the text --SEQ ID NO:2--.

In Claim 9, at Column 28, Line 34, delete the text "SEQ ID NO:5" and replace it with the text --SEQ ID NO:2--.

Signed and Sealed this
Second Day of October, 2018

Andrei Iancu
*Director of the United States Patent and Trademark Office*